(12) United States Patent
Kidd et al.

(10) Patent No.: US 9,863,002 B2
(45) Date of Patent: Jan. 9, 2018

(54) GENETIC DETERMINANTS OF PROSTATE CANCER RISK

(71) Applicants: University of Louisville Research Foundation, Louisville, KY (US); North Carolina Central University, Durhma, NC (US)

(72) Inventors: La Creis Renee Kidd, Louisville, KY (US); Kevin Sean Kimbro, Durham, NC (US)

(73) Assignees: North Carolina Central University, Durham, NC (US); University of Louisville Research Foundation, Louisville, KY (US)

( * ) Notice: Subject to any disclaimer, the term of this patent is extended or adjusted under 35 U.S.C. 154(b) by 443 days.

(21) Appl. No.: 13/907,779

(22) Filed: May 31, 2013

(65) Prior Publication Data
US 2013/0323734 A1    Dec. 5, 2013

Related U.S. Application Data

(60) Provisional application No. 61/655,243, filed on Jun. 4, 2012.

(51) Int. Cl.
*C12Q 1/68* (2006.01)
*C12P 19/34* (2006.01)

(52) U.S. Cl.
CPC ..... *C12Q 1/6886* (2013.01); *C12Q 2600/156* (2013.01); *C12Q 2600/172* (2013.01)

(58) Field of Classification Search
None
See application file for complete search history.

(56) References Cited

PUBLICATIONS

An et al., "Modulating influence on HIV/AIDS by interacting RANTES gene variants," Proc Natl Acad Sci U.S.A, 2002, 99:10002-7.
Blanpain et al., "A chimeric MIP-1alpha/RANTES protein demonstrates the use of different regions of the RANTES protein to bind and activate its receptors," J Leukoc Biol., 2001, 69:977-85.
Bracci et al., "Chemokine polymorphisms and lymphoma: a pooled analysis," Leuk Lymphoma, 2010, 51:497-506 (Author Manuscript).
Chang et al., "Stromal cell-derived factor-1 but not its receptor, CXCR4, gene variants increase susceptibility and pathological development of hepatocellular carcinoma," Clin Chem Lab Med., 2009, 47(4):412-8.
Coussens et al., "Inflammation and cancer," Nature, 2002, 420:860-7 (Author Manuscript).
Duell et al., "Inflammation, genetic polymorphisms in proinflammatory genes TNF-A, RANTES, and CCR5, and risk of pancreatic adenocarcinoma," Cancer Epidemiol Biomarkers Prev., 2006, 15:726-31.
Enjuanes et al., "Genetic variants in apoptosis and immunoregulation-related genes are associated with risk of chronic lymphocytic leukemia," Cancer Res., 2008, 68:10178-86.
Fellay et al., "Common genetic variation and the control of HIV-1 in humans," PLoS Genetics, 2009, 5(12):e1000791, 12 pages.
Hirata et al., "CXCL12 G801A polymorphism is a risk factor for sporadic prostate cancer susceptibility," Clin Cancer Res., 2007, 13(17):5056-62.
Konig et al., "Analysis of the inflammatory network in benign prostate hyperplasia and prostate cancer," Prostate, 2004, 58(2):121-9.
Liou et al., "RANTES-403 polymorphism is associated with reduced risk of gastric cancer in women," J Gastroenterol., 2008, 43(2):115-23.
Luster et al., "Chemokines—chemotactic cytokines that mediate inflammation," N Engl J Med., 1998, 338:436-45.
Manes et al., "CCR5 expression influences the progression of human breast cancer in a p53-dependent manner," J Exp Med., 2003, 198(9):1381-9.
Manolio et al., "Finding the missing heritability of complex diseases," Nature, 2009, 461(7265):747-53 (Author Manuscript).
McCarthy et al., "Genome-wide association studies for complex traits: consensus, uncertainty and challenges," Nature Rev Genet., 2008, 9(5):356-69.
Moore et al., "Distinct CXC chemokines mediate tumorigenicity of prostate cancer cells," Am J Pathol., 1999, 154(5):1503-12.
Petersen et al., "No association between common chemokine and chemokine receptor gene variants and prostate cancer risk," Cancer Epidemiol Biomarkers Prev., 2008, 17(12):3615-7.
Purdue et al., "Variation in innate immunity genes and risk of multiple myeloma," Hematol Oncol., 2011, 29(1):42-6 (Author Manuscript).
Reiland et al., "CXC-chemokines stimulate invasion and chemotaxis in prostate carcinoma cells through the CXCR2 receptor," Prostate, 1999, 41(2):78-88.
Rollins et al., "Chemokines," Blood, 1997, 90(3):909-28.
Saenz-Lopez et al., "Genetic polymorphisms of RANTES, ILI-A, MCP-1 and TNF-A genes in patients with prostate cancer," BMC Cancer, 2008, 8:382, 8 pages.
Soria and Ben-Baruch, "The CCL5/CCR5 Axis in Cancer," Human Press, New York, 2009, pp. 109-130.
Stricter et al., "The functional role of the ELR motif in CXC chemokine-mediated angiogenesis," J Biol Chem., 1995, 270(45):27348-57.
Strieter et al., "CXC chemokines in angiogenesis," Cytokine Growth Factor Rev, 2005, 16(6):593-609.
Taichman et al., "Use of the stromal cell-derived factor-1/CXCR4 pathway in prostate cancer metastasis to bone," Cancer Res., 2002, 62(2):1832-7.
Vaday et al., "Expression of CCL5 (RANTES) and CCR5 in prostate cancer," Prostate, 2006, 66:124-34.
Vindrieux et al., "Emerging roles of chemokines in prostate cancer," Endocrine-related cancer, 2009, 16(3):663-73.
Weng et al., "Effect of CC chemokine ligand 5 and CC chemokine receptor 5 genes polymorphisms on the risk and clinicopathological development of oral cancer," Oral Oncol., 2010, 46(10):767-72.
Zhernakova et al., "Genetic variants of RANTES are associated with serum RANTES level and protection for type 1 diabetes," Genes Immun., 2006, 7(7):544-9.

*Primary Examiner* — Jehanne Sitton
(74) *Attorney, Agent, or Firm* — Fish & Richardson P.C.

(57) ABSTRACT

Described are methods of determining if a subject has a genetic predisposition to developing prostate cancer (PCa), e.g., an American or Caribbean subject of African descent and of reducing their risk.

11 Claims, 1 Drawing Sheet

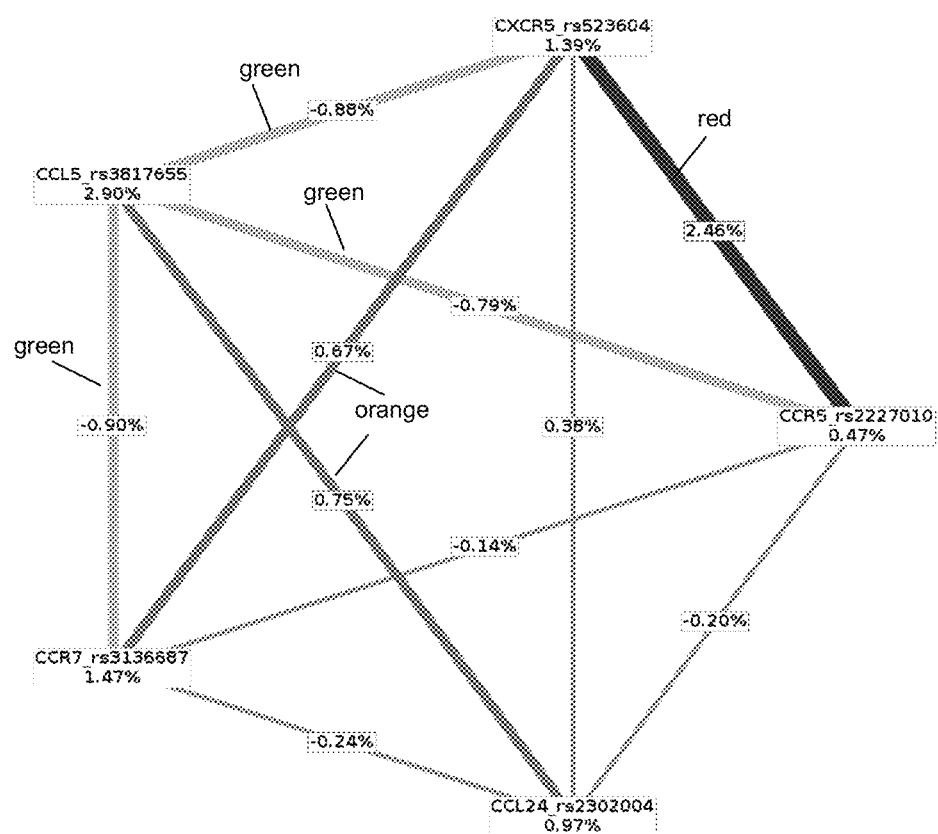

GENETIC DETERMINANTS OF PROSTATE CANCER RISK

CLAIM OF PRIORITY

This application claims the benefit of U.S. Provisional Patent Application No. 61/655,243, filed on Jun. 4, 2012. The entire contents of the foregoing are incorporated by reference herein.

FEDERALLY SPONSORED RESEARCH OR DEVELOPMENT

This invention was made with Government support under Grant No. P20-MD000175 awarded by the National Institutes of Health. The Government has certain rights in the invention.

TECHNICAL FIELD

This invention relates to methods for predicting risk of developing prostate cancer, aggressive prostate cancer, or breast cancer, using genetic variants in in chemokines/chemokine receptors including chemokine (C-C motif) ligand 5 (CCL5), chemokine (C-C motif) receptor 5 (CCR5), or chemokine (C-C motif) receptor 7 (CCR7) genes.

BACKGROUND

Recent studies have revealed participation of chemokines (e.g., CC, CXC, XCL, and C-X3-C gene families) in cancer by regulating leukocyte movement to modify local immunoresponse. Chemokines have multifaceted roles: they attract cancer cells and chemokine receptor bearing cells, especially T and dendritic cells; they facilitate dendritic cell functions; and they exert an angiostatic effect. Chemokines play a pivotal role in chemotaxis, leukocyte trafficking, lymphocyte development, angiogenesis, host response to infection, inflammatory processes, as well as tumor development, migration and metastasis. Chemokines mediate their actions through 7-transmembrane, G protein coupled receptors and serve three major physiological functions. First, they play fundamental roles in the maturation, homeostasis and function of the immune system, and facilitate the trafficking of memory T cells, lymphocytes, monocytes, and neutrophils to the inflammatory site. Secondly, they display chemotactic activity for lymphocytes, monocytes, and neutrophils. Lastly, they attract cancer cells and chemokine receptor bearing cells and have effects on endothelial cells involved in angiogenesis regulation. Several CXC chemokines are potent angiogenesis promoters (i.e., CXCL1, 2, 3, 5, 6, 7) (Luster et al., (1998) The New England Journal of Medicine, 338, 436-45; Rollins et al., (1997) Blood, 90, 909-28; Strieter et al., (2005) Cytokine & growth factor reviews, 16, 593-609); whereas, others inhibit angiogenesis (i.e., CXCL4, 9, 10, 11) (Strieter et al., (1995) The Journal of Biological Chemistry, 270, 27348-57).

SUMMARY

The present invention is based, at least in part, on the discovery that polymorphisms in chemokine-associated genes modify PCA susceptibility, e.g., among men of African descent; thus, chemokine-related markers can be used as significant predictors of prostate cancer, e.g., among men of African descent, including African-Americans and African-Carribeans.

Thus, the invention includes methods for determining a subject's risk of developing PCa, based on detection of those allelic variants.

In one aspect, the invention includes methods for determining a subject's risk for developing PCa. The methods can include obtaining a sample comprising genomic DNA (gDNA) from the subject, and determining the identity, absence or presence of polymorphisms as described herein. In some embodiments, the methods include obtaining a test haplotype for the subject comprising polymorphisms of CCL5, CCL25, CCR5, CCR7, CCR9, CXCR2, and/or CXCR7, wherein the haplotype provides information regarding the subject's risk of developing PCa. In some embodiments, the presence of an allele or haplotype shown in Table A indicates that the subject has an increased risk of developing PCa, and the presence of an allele or haplotype shown in Table B, indicates that the subject has a decreased risk of developing PCa.

TABLE A

Genotypes associated with an increase in PCA risk

| Gene | SNP | SEQUENCE | SEQ ID NO: | Genotype associated with increased risk |
|------|-----|----------|------------|------------------------------------------|
| CCR5 | rs1799988 | taatccagtgagaaaagcccgtaaataaac[c/t]ttcagaccagagatctattctctagcttat | 1 | CC |
| CCR5 | rs1799987 | ggggatacggggagagtggagaaaaggggg[a/g]cacagggttaatgtgaagtccaggatcccc * | 2 | AA |
| CCR7 | rs3136685 | tcattttgtgtaacagaaaccctccctcct [c/t]acccacctcttgctccttgctgggcagatg * | 3 | TC + CC |

TABLE A -continued

Genotypes associated with an increase in PCA risk

| Gene | SNP | SEQUENCE | SEQ ID NO: | Genotype associated with increased risk |
|---|---|---|---|---|
| CCR7 | rs3136687 | ggaaagaaaattattggctggctgccccca [c/t] ctccaaaccatgaacttccatccccacatt * | 4 | TC |
| CXCR2 | rs1045879 | agcagcaccgccacgtggtagggca[a/g] ccagcagacaggaaagaccaccactg | 5 | AG + GG |

* reverse/bottom strand sequence

TABLE B

Genotypes associated with a reduction in PCA risk

| Gene | SNP | SEQUENCE | SEQ ID NO: | Genotype associated with decreased risk |
|---|---|---|---|---|
| CCL5 | rs2107538 | taacatccttccatggatgagggaaaggag [a/g] taagatctgtaatgaataagcaggaactt * | 6 | AA |
| CCL5 | rs3817655 | ttctggcttggagcccttttgatccaacaga [a/t] gaggaaatgttctctccttaaaagccacaa | 7 | TA + AA |
| CCL25 | rs2032887 | atgctcgaaataaggtttttgcaaagctcc [a/g] ccacaacacgcagaccttccaaggtgggca | 8 | AG + GG |
| CCL5 | rs2107538 | taacatccttccatggatgagggaaaggag [a/g] taagatctgtaatgaataagcaggaactt * | 9 | GA + AA |
| CCL5 | rs2280789 | acacctgtaggccttgagggtgtagacctt [a/g] aagacagaaaaactgatcaggagatccctg * | 10 | AG |
| CCR9 | rs1488371 | tatgattgccaacagcacccctcaagggct [a/c] ttcctccaaatttctatgagaccttgaacc | 11 | CA + AA |

* reverse/bottom strand sequence

In one aspect, the invention provides methods for determining risk of developing prostate cancer (PCa) in a subject of African descent. The methods include optionally selecting a subject who is suspected of being at risk of developing PCa; obtaining a sample comprising DNA of the subject; and detecting in the sample the presence of a genetic profile comprising one, two or more alleles, genotypes, or haplotypes listed in Tables 4-9, A, or B in the subject. The presence of alleles that are associated with an increased risk of developing PCa indicates that the subject has an increased risk of developing PCa, and the presence of alleles, genotypes, or haplotypes that are associated with a decreased risk of developing PCa indicates that the subject has a decreased risk of developing PCa, as compared to a subject lacking the alleles, genotypes, or haplotypes.

In some embodiments, the presence of one or more of
(i) a TA or AA genotype at rs3817655;
(ii) a GA or AA genotype at rs2107538;
(iii) an AG or GG genotype at rs2032887, e.g., in an African-American man;
(iv) an AG or GG genotype at rs2032887,
(v) a GA or AA genotype at rs2107538;
(vi) an AG genotype at rs2280789, e.g., in an African-American man; or
(vii) a CA or AA genotype at rs1488371, e.g., in a Caribbean man,
indicates that the subject has a decreased risk of developing PCa as compared to a subject who does not have the genotype.

In some embodiments, the presence of one or more of:
(i) a CC genotype at rs1799988;
(ii) an AA genotype at rs1799987, e.g., in a Caribbean man;
(iii) a TC or CC genotype at rs3136685;
(iv) a TC genotype at rs3136687; or
(v) an AG or GG genotype at rs1045879, e.g., in an African-American man,
indicates that the subject has a decreased risk of developing PCa as compared to a subject who does not have the genotype.

In some embodiments, the methods include identifying the subject as having increased or decreased risk based on the genetic profile.

In some embodiments, the subject has an enlarged but not cancerous prostate, e.g., benign prostatic hyperplasia, and the subject has been identified as having a decreased risk of PCa, the method further comprising treating the subject conservatively, e.g., by watchful waiting.

In some embodiments, the subject has been identified as having an increased risk of PCa, further comprising one or more of: determining that the subject has an increased risk based on the presence of an allele or genotype described herein; diagnosing or identifying the subject as having increased risk; assigning a level of risk to the subject based on the presence of the allele or genotype; advising the subject that they have an increased risk of developing PCa or aggressive PCa, and optionally instructing the subject to perform self-monitoring of symptoms and/or self-evaluation of prostate tissues; advising the subject that their family members may also have an increased risk of developing PCa or aggressive PCa; advising the subject's family members that they may also have an increased risk of developing PCa or aggressive PCa, and optionally determining the identity of the allele or genotype associated with risk of developing PCa or aggressive PCa present in the subject in one or more family members; advising the subject to request additional monitoring or treatment for PCa; providing information to the subject regarding their increased risk of developing PCa or aggressive PCa; noting the subject's risk level and/or the identity of the allele or genotype detected in a database or medical history; informing the subject's health care provider that the subject has an increased risk; modifying a database or the subject's medical history to indicate the allele or genotype and/or risk of developing PCa or aggressive PCa; selecting the subject for a prophylactic treatment (e.g., to decrease risk); selecting the subject for increased monitoring, e.g., monitoring that is begun earlier or occurs more frequently than in subjects who do not have increased risk; monitoring the subject for development of PCa, e.g., by one or more of self-examination, self-monitoring for one or more symptoms of PCa as known in the art, examination by a health care provider, performing an imaging study to detect the development of PCa, performing one or more blood tests, e.g., to detect levels of Prostate Serum Antigen (PSA) that are associated with PCa, performing a biopsy to detect cancerous cells; selecting the subject for inclusion in a clinical trial; and/or excluding the subject from inclusion in a clinical trial.

In some embodiments, the subject has been identified as having an increased risk of PCa, further comprising administering a treatment to the subject, e.g., a prophylactic treatment, e.g., to decrease their risk of developing PCa, or a treatment for PCa.

In some embodiments, the subject has been identified as having an increased risk of PCa, further comprising administering a treatment for PCa to a subject who has been identified as having an increased risk of developing PCa.

In some embodiments, the subject is a human.

In some embodiments, the subject is a patient having one or more risk factors for PCa. In some embodiments, the risk factors associated with PCa include one or more of: age; race/ethnicity; nationality; family history; diet; obesity; lack of exercise; inflammation of the prostate; infection; vasectomy in men; and the presence of other genes or genetic variants associated with increased risk of PCa.

In some embodiments, the subject has one or more of a grandparent, parent, uncle or aunt, sibling, or child who has or had PCa.

In some embodiments, where the subject has been identified using a method described herein as having an increased risk of PCa or aggressive PCa, the methods include one or more of: determining that the subject has an increased risk based on the presence of an allele or genotype described herein; diagnosing or identifying the subject as having increased risk; assigning a level of risk to the subject based on the presence of the allele or genotype; advising the subject that they have an increased risk of developing PCa or aggressive PCa, and optionally instructing the subject to perform self-monitoring of symptoms and/or self-evaluation of prostate tissues; advising the subject that their family members may also have an increased risk of developing PCa or aggressive PCa; advising the subject's family members that they may also have an increased risk of developing PCa or aggressive PCa, and optionally determining the identity of the allele or genotype associated with risk of developing PCa or aggressive PCa present in the subject in one or more family members; advising the subject to request additional monitoring or treatment for PCa; providing information to the subject regarding their increased risk of developing PCa or aggressive PCa; noting the subject's risk level and/or the identity of the allele or genotype detected in a database or medical history; informing the subject's health care provider that the subject has an increased risk; modifying a database or the subject's medical history to indicate the allele or genotype and/or risk of developing PCa or aggressive PCa; selecting the subject for a prophylactic treatment (e.g., to decrease risk); selecting the subject for increased monitoring, e.g., monitoring that is begun earlier or occurs more frequently than in subjects who do not have increased risk; monitoring the subject for development of PCa, e.g., by one or more of self-examination, self-monitoring for one or more symptoms of PCa as known in the art, examination by a health care provider, performing an imaging study to detect the development of PCa, performing one or more blood tests, e.g., to detect levels of Prostate Serum Antigen (PSA) that are associated with PCa, performing a biopsy to detect cancerous cells; selecting the subject for inclusion in a clinical trial; and/or excluding the subject from inclusion in a clinical trial. In some embodiments, the methods further include administering a treatment to the subject, e.g., a prophylactic treatment, e.g., to decrease their risk of developing PCa, or a treatment for PCa. In some embodiments, the methods include surgical removal of the prostate. In some embodiments, where the subject has PCa and has been identified as being at increased risk of developing aggressive disease by a method described herein, the methods further include administering a treatment for PCa as known in the art, e.g., surgical removal of the prostate. In some embodiments, the methods include selectively administering a treatment for PCa to a subject who has been identified as having an increased risk of developing PCa or aggressive PCa.

In some embodiments, where the subject has been identified using a method described herein as having a decreased risk of PCa or aggressive PCa, the methods include one or more of: determining that the subject has a decreased risk based on the presence of an allele or genotype described herein; diagnosing or identifying the subject as having a decreased risk; advising the subject that they have a decreased risk of developing PCa or aggressive PCa; advising the subject that they have a decreased risk of developing PCa or aggressive PCa, and optionally instructing the subject to perform self-monitoring of symptoms and/or self-evaluation of prostate tissues; advising the subject that their family members may also have a decreased risk of developing PCa or aggressive PCa; advising the subject's family members that they may also have a decreased risk of developing PCa or aggressive PCa, and optionally determining the identity of the allele or genotype associated with risk of developing PCa or aggressive PCa present in the subject in one or more family members; providing information to the subject regarding their decreased risk of developing PCa or aggressive PCa; assigning a level of risk to the subject based on the presence of the allele or genotype; noting the subject's risk level in a database or medical history; informing the subject's health care provider that the subject has an increased risk; modifying a database or the subject's medical history to indicate the allele or genotype and risk of developing PCa or aggressive PCa; selecting the subject for decreased monitoring, e.g., monitoring that is begun later or occurs less frequently than in subjects who have increased risk; selecting the subject for inclusion in a clinical trial; and/or excluding the subject from inclusion in a clinical trial. In some embodiments, where the subject has PCa and has been identified as being at decreased risk of developing aggressive disease by a method described herein, the methods further include treating the subject conservatively, e.g., by watchful waiting.

In some embodiments, the methods further include administering a treatment to the subject to decrease their risk of developing PCa or to treat PCa. In some embodiments, the methods include surgical removal of the prostate.

Information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in a clinical trial, e.g., a trial of a treatment for PCa. The methods include obtaining a haplotype for the subject including one, two or more of the polymorphisms described herein; determining whether the genetic profile is associated with an increased risk of developing PCa; and including the subject in the trial if the genetic profile indicates that the subject has (or does not have) an increased risk of developing PCa.

In another aspect, the invention provides methods for selecting a subject for administration of a treatment for PCa. The methods include obtaining a genetic profile for the subject, wherein the genetic profile comprises one, two or more of the polymorphisms described herein; determining whether the genetic profile is associated with an increased risk of developing PCa; and administering the treatment to the subject if the genetic profile indicates that the subject has an increased risk of developing PCa.

In another aspect, the invention provides methods for selecting a treatment for administration to a subject. The methods include obtaining a genetic profile for the subject, wherein the genetic profile includes one, two or more of the polymorphisms described herein; determining whether the genetic profile is associated with an increased risk of developing PCa; and administering the treatment for PCa to the subject if the genetic profile indicates that the subject has an increased risk of developing PCa.

In some embodiments of the methods described herein, the subject is of European descent.

As used herein, the terms "increased" or "decreased" risk is determined relative to subjects with the referent allele or genotype, or lacking the specified allele or genotype (as shown herein, e.g., in Tables A, B, or 4-9).

Also provided herein are kits for use in detection of genetic profiles associated with PCa, including at least one nucleic acid probe that hybridizes to a sequence that includes a polymorphism described herein, or can be used to amplify a sequence that includes a polymorphism described herein.

Also provided are arrays that include a substrate having a plurality of addressable areas, wherein one or more of the addressable areas includes one or more probes that can be used to detect a polymorphism described herein.

As used herein, a "genetic profile" is one or a set of signature genetic changes (e.g., polymorphisms). A "genetic profile" as used herein is information regarding the presence or absence of one or more genetic markers in a subject. A genetic profile can consist of a variety of genetic markers, including indels (insertions or deletions of the DNA at particular locations on the chromosome); single nucleotide polymorphisms (SNPs) in which a particular nucleotide is changed; microsatellites; and minisatellites. A "haplotype" is one or a set of signature genetic changes (i.e., a genetic profile) that includes markers that are normally grouped closely together on the DNA strand, and are usually inherited as a group;

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional and internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that encodes a gene product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intra-specific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or genetic profiles described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a graphical model describing the percent entropy that is explained by each Chemokine-Related SNP or a combination of two loci within the present study population. Positive percent entropy indicates information gain or synergy. However, negative percent indicates redundancy or lack of information gain. Schematic visualization represents a continuum from synergy (i.e. non-additive) to redundancy, ranging from a high degree of synergy (labeled "high", representing positive information gain), a lesser degree of synergy (labeled "low"), and the unlabeled, narrow lines represent independence and a midway point between synergy and redundancy. On the other hand, lines labeled "redundant" represent redundancy.

DETAILED DESCRIPTION

Chemotaxis is an important process required for tumor growth and metastasis. It is regulated by a complex network of chemokines, chemokine receptors and downstream targets that synergistically regulate immune and inflammatory responses. Recent molecular studies have demonstrated that over expression of selected chemokines and chemokine receptors are related to aggressive cancer phenotypes, including lung, breast and prostate cancer. Some observational studies suggest inheritance of susceptibilities detected in chemokine associated genes may alter the risk of developing cancer. However, to the present inventors' knowledge, there are no published reports on the impact of inheriting multiple functional variants in relation to prostate cancer among men of African Descent. Therefore, the current study evaluated the individual and combined effects of 43 chemokine associated sequence variants on PCA risk among 279 cases and 535 disease-free men of African descent from the U.S. and Jamaica using LR MDR modeling. Five SNPs detected in CCL5, CCR5 and CCR7 were significantly associated with prostate cancer risk among all study participants; however, only three markers survived adjustments for potential confounders and multiple hypothesis testing. Notably, inheritance of at least one CCL5 rs3817655 A or CCL5 rs2107538 A loci was linked with a 34-44% decrease in PCA susceptibility among all men of African Descent. In addition, the recessive genetic model for CCR5 rs1799988 was associated with a 52-73% increase in PCA risk. There were significant main effects for the CCL5 rs3817655 and CCR7 rs3136685 SNPs among U.S. and Jamaican men, respectively. A complex interaction among CCR5 rs2227010, CCR7 rs3136687, and CXCR5 rs523604 served as an important predictor of prostate cancer; however, this interaction appears to be additive in nature.

Several cancer cells, including PCA cells, express chemokines and their cell surface bound receptors. Chemokine ligand 5 (RANTES), is a small molecule with a strong capacity to induce cellular migration of inflammatory cells and production of its receptor (CCR5) in human PCA cell lines [16,44]. The CCL5/CCR5 axis induces PCA cell proliferation and cell invasion. It's speculated that once CCL5 binds to CCR5, it serves as an autocrine factor and activates cellular responses involved in cancer progression [16]. In the current study, possession of the CCL5 rs3817655 A or CCL5 rs2107538 A loci was linked with a protective effect in relation to prostate cancer risk among all men of African descent from the U.S. and Jamaica combined. The directionality of the risk estimates persisted when we stratified by racial/ethnic group; however, the findings were only statistical significant for the U.S. men. In addition, findings for the total and U.S. subgroups remained significant even after adjusting for age and multiple hypothesis testing. The observed protective effects associated with the two aforementioned CCL5 SNPs (rs3817655, rs2107538) may be attributed to a reduction in transcriptional activation, reduced protein levels, and ultimately reduced tumorigenic capacity. There are no published reports on the impact of the CCL5 rs3817655 SNP on prostate cancer susceptibility or its functional consequence on genes/proteins. The CCL5 rs2107538 G-403A promoter SNP is associated with a decrease in protein expression detected in serum collected from Type II diabetic and disease-free subjects [19]. In addition, this loci has been evaluated in two independent prostate cancer studies. In a study involving 607 Caucasian male residents of Spain (297 cases, 3011 controls), Saenz-Lopez and co-workers (2008) observed a 1.44-fold increase in PCA risk among carriers of the CCL5 rs2107538 GA+AA genotype (P=0.039) [21]. However, this finding did not corroborate with a larger null report consisting of 1553 Caucasian men (i.e., 815 PCA cases, 738 controls) from Australia [45]. The present findings of a protective effect against PCA among the study participants is consistent with other published reports that reveal a decrease in the risk of developing gastric cancer, lymphoma, and type 1 diabetes [10,19,46]. Within a multi-ethnic pancreatic case-control study, the prevalence of the "A" allele was more frequent among disease-free Asian and African-Americans relative to pancreatic cases [23]; however, this allele was more prevalent among Caucasian pancreatic cases relative to controls.

The functional impact of CCL5 sequence variants is complicated by the high degree of linkage disequilibrium within both the promoter and intron 1 region. An and co-workers (2006), evaluated the impact of three SNPs detected in the promoter region (rs2280788-28C/G, rs2107538-405 G/A) and intron 1 of CCL5 rs2280789 [20]. They demonstrated that transcriptional regulation of CCL5 was primarily governed by an intron 1.1 T/C SNP (rs2280789). Intron 1.1 C allele corresponded with a strong decrease in transcriptional activity of RANTES, whereas the −28G allele had modest up-regulation in human cell lines. In the stratified analysis described herein, the intron 1.1 CCL5 rs2280789 C allele was associated with a marginal 36-41% decrease in PCA risk among men of African descent from the US; however, these findings require further evaluation in a larger study set. The CCL5 rs2280788-28C/G was not evaluated in the current study, since C allele frequency is 0% for African-American men as reported in NCBI. The functional consequence of CCL5 SNPs is further complicated by its interaction with downstream receptors.

The biological activity mediated by CCL5 is facilitated through its interaction with chemokine receptors (CCR1, CCR2, CCR3, and CCR5). However, relative to CCR1-3, CCR5 plays a more important role in CCL5-mediated cell migration [47]. CCR5, a member of the beta chemokine receptor family, is a seven transmembrane protein, which is expressed by T cells and macrophages. Over expression of CCR5 has been detected in aggressive prostate cancer tissue relative to benign prostatic hyperplasia [44]. The CCR5 rs1799988 C allele is significantly associated with viral load set point (i.e., decreased time from asymptomatic HIV+ to AIDS and increased infectiousness) and AIDS progression [48]; however, there are no published reports for this 5'UTR SNP in relation to prostate cancer or other inflammatory/immune response-related diseases. In the current study, a 1.5-1.75 fold increase in the risk of developing prostate cancer was observed among all men of African descent who possessed the CCR5 rs1799988 CC genotype. However, the impact of this SNP in relation to PCA risk was more pronounced among men of African descent from Jamaica relative to U.S. men. This increased risk may have an impact on transcriptional activity, which may result in increased protein levels of CCR5; however, this requires confirmation using ex vivo, in vitro, and micro-dissected tumor tissue-based assays.

Forty-three sequence variants were evaluated in relation to prostate cancer risk among men of African descent from the U.S. and Jamaica. A strong correlation between the minor allele frequencies between these two study populations enabled pooling of genetic data to identify relationships that would have remained undetected if the populations were evaluated separately. As a result of pooling, three SNPs (i.e., CCL5 rs3817655, CCL5 rs2107538, CCR5 rs1799988) were identified that were significantly associated with prostate cancer in the total population even after adjusting for age and multiple hypothesis testing. Upon stratification by study center, the possibility that race/ethnic specific sequence variants may track with disease progression or prognosis cannot be ruled out. The exploratory analysis in the current study suggests selected chemokines and receptors are associated with high tumor grade (data not shown).

Study participants in the current study self-identified themselves as African-American, Caribbean, African, or Jamaican. Population admixture, which commonly occurs among men of African descent, may bias risk estimates. Adjustments of risk estimates for West African Ancestry and family history did not modify the results among the U.S. and Jamaican men, respectively. Although the possibility of population stratification among Jamaican men cannot be excluded, a strong correlation in the minor allele frequency between men from the U.S. and Jamaica suggest that admixture will not significantly modify relationships observed between the SNPs and PCA risk.

Methods of Diagnoses and Evaluation of Risk

Described herein are a variety of methods for the diagnosis of susceptibility to PCa. "Susceptibility" does not necessarily mean that the subject will develop PCa, but rather that the subject is, in a statistical sense, more likely to develop PCa than a member of the general population, i.e., has an increased risk of developing PCa. As used herein, susceptibility to PCa exists if the subject has a genetic profile associated with an increased risk of PCa as described herein. Ascertaining whether the subject has such a genetic profile is included in the concept of diagnosing susceptibility to PCa as used herein. Such determination is useful, for example, for purposes of diagnosis, treatment selection, and genetic counseling. Thus, the methods described herein can include obtaining a genetic profile associated with an increased risk of PCa as described herein for the subject.

As used herein, "obtaining a genetic profile" includes obtaining information regarding the identity, presence or absence of one or more genetic markers in a subject. Obtaining a genetic profile can, but need not, include obtaining a sample comprising DNA from a subject, and/or assessing the identity, presence or absence of one or more genetic markers in the sample. The individual or organization who obtains the genetic profile need not actually carry out the physical analysis of a sample from a subject; the genetic profile can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Obtaining a genetic profile can also include or consist of reviewing a subject's medical history, where the medical history includes information regarding the identity, presence or absence of one or more genetic markers in the subject, e.g., results of a genetic test.

In some embodiments, to detect the presence of a genetic profile described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for PCa if the subject has an increased risk of developing PCa. As another example, a drug or treatment may be indicated for individuals with a certain genetic profile, and the insurance company would only reimburse the health care provider (or the insured individual) for prescription or purchase of the drug if the insured individual has that genetic profile. The presence or absence of the genetic profile in a patient may be ascertained by using any of the methods described herein.

Information gleaned from the methods described herein can also be used to select or stratify subjects for a clinical trial. For example, the presence of a selected genetic profile described herein can be used to select a subject for a trial. The information can optionally be correlated with clinical information about the subject, e.g., diagnostic or endophenotypic information.

Genetic Profiles Associated with PCa

As described herein, genetic profiles associated with PCa include those alleles listed in Tables A, B, and 4-9.

Linkage Disequilibrium Analysis

Linkage disequilibrium (LD) is a measure of the degree of association between alleles in a population. One of skill in the art will appreciate that genetic profiles involving markers within 1 Linkage Disequilibrium Unit (LDU) of the polymorphisms described herein can also be used in a similar manner to those described herein. LDUs share an inverse relationship with LD so that regions with high LD (such as haplotype blocks) have few LDUs and low recombination, whilst regions with many LDUs have low LD and high recombination. Methods of calculating LDUs are known in the art (see, e.g., Morton et al., Proc Natl Acad Sci USA 98(9):5217-21 (2001); Tapper et al., Proc Natl Acad Sci USA 102(33):11835-11839 (2005); Maniatis et al., Proc Natl Acad Sci USA 99:2228-2233 (2002)).

Thus, in some embodiments, the methods include analysis of polymorphisms that are within 1 LDU of a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African-Americans would ideally be used to identify markers within 1 LDU of a marker described herein for use in genotyping a subject of African American descent.

Alternatively, methods described herein can include analysis of polymorphisms that are within a value defined by Lewontin's D' (linkage disequilibrium parameter, see Lewontin, Genetics 49:49-67 (1964)) of a polymorphism described herein. Results can be obtained, e.g., from on line public resources such as HapMap.org. The simple linkage disequilibrium parameter (D) reflects the degree to which alleles at two loci (for example two SNPs) occur together more often (positive values) or less often (negative values) than expected in a population as determined by the products of their respective allele frequencies. For any two loci, D can vary in value from −0.25 to +0.25. However, the magnitude of D (Dmax) varies as function of allele frequencies. To control for this, Lewontin introduced the D' parameter, which is D/Dmax and varies in value from −1 (alleles never observed together) to +1 (alleles always observed together).

Typically, the absolute value of D' (i.e., |D'|) is reported in online databases, because it follows mathematically that positive association for one set of alleles at two loci corresponds to a negative association of equal magnitude for the reciprocal set. This disequilibrium parameter varies from 0 (no association of alleles at the two loci) to 1 (maximal possible association of alleles at the two loci).

Thus, in some embodiments, the methods include analysis of polymorphisms that are within D'>0.75, or D'=1, for pairwise comparisons, of a polymorphism described herein.

Methods of Determining the Presence or Absence of a Genetic Profile Associated with Risk of Developing PCa The methods described herein include determining the presence or absence of genetic profiles associated with PCa. In some embodiments, an association with PCa is determined by the presence of a shared genetic profile between the subject and an affected reference individual, e.g., a first or second-degree relation of the subject, and the absence of the genetic profile in an unaffected reference individual. Thus the methods can include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a genetic profile associated with PCa as described herein can be determined using methods known in the art, e.g., gel electrophoresis, capillary electrophoresis, size exclusion chromatography, sequencing, and/or arrays to detect the presence or absence of the marker(s) of the genetic profile. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications*, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a genetic profile as described herein. The genetic profile can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)-glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of PCa.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to PCa.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to PCa) to DNA from the subject is indicative of susceptibility to PCa.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997).

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence comprising a polymorphism described herein, and can be used to detect the absence or presence of said polymorphism, e.g., one or more SNPs, microsatellites, minisatellites, or indels, as described herein, to determine a genetic profile. For example, the array can include one or more nucleic acid probes that can be used to detect a polymorphism listed in Tables 1-3. In some embodiments, the array further includes at least one area that includes a nucleic acid probe that can be used to specifically detect another marker associated with PCa, as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 4p and/or 22q, e.g., a region between SNP rs801720 and SNP rs710123, e.g., a region between SNP rs713692 and rs756638, optionally, a different portion of genomic DNA, e.g., a portion that includes a different portion of human chromosomes 22 and/or 4, or another chromosome, e.g., including another region associated with PCa., and detecting binding of a nucleic acid from the sample to the array. Optionally, the method includes amplifying nucleic acid from the sample, e.g., genomic DNA that includes a portion of a human chromosome described herein, and, optionally, a region that includes another region associated with PCa, prior to or during contact with the array.

In some aspects, the methods described herein can include using an array that can ascertain differential expression patterns or copy numbers of one or more genes in samples from normal and affected individuals (see, e.g., Redon et al., Nature. 444(7118):444-54 (2006)). For example, arrays of probes to a marker described herein can be used to measure polymorphisms between DNA from a subject having PCa, and control DNA, e.g., DNA obtained from an individual that does not have PCa, and has no risk factors for PCa. Since the clones on the array contain sequence tags, their positions on the array are accurately known relative to the genomic sequence. Different hybridization patterns between DNA from an individual afflicted with PCa and DNA from a normal individual at areas in the array corresponding to markers in a human chromosome as described herein, and, optionally, one or more other regions associated with PCa, are indicative of a risk of PCa. Methods for array production, hybridization, and analysis are described, e.g., in Snijders et al., (2001) *Nat. Genetics* 29:263-264; Klein et al., (1999) Proc. Natl. Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002. Real time quantitative PCR can also be used to determine copy number.

In another aspect, the invention features methods of determining the absence or presence of a genetic profile associated with PCa as described herein, using an array described above. The methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for PCa, and comparing the binding of the first sample with one or more references, e.g., binding of a sample from a subject who is known to have PCa, and/or binding of a sample from a subject who is unaffected, e.g., a control sample from a subject who neither has, nor has any risk factors for PCa. In some embodiments, the methods include contacting the array with a second sample from a subject who has PCa; and comparing the binding of the first sample with the binding of the second sample. In some embodiments, the methods include contacting the array with a third sample from a cell or subject that does not have PCa and is not at risk for PCa; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Prostate Cancer (PCa)

PCa is an uncontrolled (malignant) growth of cells in the prostate gland which is located at the base of the urinary bladder and is responsible for helping control urination as well as forming part of the semen. Prostate cancer is the second leading cause of death of males in the U.S. The methods described herein can be used to determine an individual's risk of developing PCa.

A number of risk factors for PCa are known in the art, including age (increased over 40, more increased over 50, highest over 65); race/ethnicity (highest in men of African descent, e.g., African American men, lower in Asian and Latino/Hispanic men); nationality (highest in North America, northwestern Europe, Australia, and Carribean, lower in Asia, Africa, Central America, and South America); family history; diet (consumption of a lot od red meat and/or high-fat dairy products increases risk); obesity (BMI>29); lack of exercise; inflammation of the prostate; infection (e.g., sexually transmitted diseases); vasectomy; and other genes (e.g., HPCa1, HPCaX, BRCA1, BRCA2, CAPB, PCaP, ELAC2/HPCa2) or genetic variants associated with increased risk of PCa (1-8).

In particular, the methods described herein are useful for determining risk of developing PCa in men of African descent, e.g., West African descent. In the US alone, nearly 31,000 cases of prostate cancer were diagnosed in African American men in 2007, which accounted for 37% of all cancers diagnosed in African American men. Despite recent improvement in treatments, PCa incidence and mortality remain higher among African American men that their white counterparts. See Odedina et al., Infect. Agents Can. 4(Suppl 1):S2 (pp. 1-8) (2009).

Current Treatment of PCa

Four treatment options are presently the standard of care: Watchful waiting (closely monitoring the subject's condition without giving any treatment until symptoms appear or change, usually used in older men with other medical problems and early-stage disease); surgery (radical prostatectomy, lymphadenectomy, transurethral resection of the prostate (TURP); orchiectomy); radiation therapy (external or internal); and hormone therapy (e.g., with LHRH agonists, antiandrogens, and estrogens). In addition, a number of experimental treatments are being evaluated in clinical trials, such as cryosurgery, chemotherapy, high-intensity focused ultrasound, and biologic therapy (e.g., using PCa-specific antibodies). Any of these treatments, or combinations thereof, can be used in the present methods.

Methods of Determining Treatment Regimens and Methods of Treating PCa

As described herein, the presence of certain genetic profiles described herein has been correlated with an increased risk of developing or having PCa, or of having aggressive PCa. Thus, the new methods can also include selecting a treatment regimen for a subject determined to be at risk for developing PCa, based upon the absence or presence of a genetic profile associated with PCa as described herein. The determination of a treatment regimen can also be based upon the absence or presence of other risk factors associated with PCa, e.g., as described herein. Therefore, the methods of the invention can include selecting a treatment regimen for a subject having one or more risk factors for PCa, and having a genetic profile described herein. The methods can also include administering a treatment regimen to a subject having, or at risk for developing, PCa to thereby treat, prevent or delay further progression of the disease.

As used herein, the term "treat" or "treatment" is defined as the application or administration of a treatment regimen, e.g., a therapeutic agent or modality, to a subject, e.g., a patient. The subject can be a patient having PCa, a symptom of PCa or at risk of developing (i.e., having one or more of the risk factors for PCa known in the art or described herein) PCa. The treatment can be to cure, heal, alleviate, relieve, alter, remedy, ameliorate, palliate, improve or affect PCa, the symptoms of PCa or the predisposition toward PCa.

The methods of the invention, e.g., methods of determining a treatment regimen and methods of treatment or prevention of PCa, can further include the step of monitoring the subject, e.g., for a change (e.g., an increase or decrease) in one or more of the diagnostic criteria for PCa listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for PCa can be evaluated by administering the same treatment or combinations or treatments to a subject having PCa and a genetic profile as described herein and to a subject that has PCa but does not have a genetic profile as described herein. The effects of the treatment or combination of treatments on each of these subjects can be used to determine if a treatment or combination of treatments is particularly effective on a sub-group of subjects having PCa. In other embodiments, various treatments or combinations of treatments can be evaluated by administering two different treatments or combinations of treatments to at least two different subjects having PCa and a genetic profile as described herein. Such methods can be used to determine if a particular treatment or combination of treatments is more effective than others in treating this subset of PCa patients.

Various treatment regimens are known in the art for treating PCa.

Pharmacogenomics

With regards to both prophylactic and therapeutic methods of treatment of PCa, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market, as detailed previously (e.g., Eichelbaum et al., Clin. Exp. Pharmacol. Physiol. 23:983-985 (1996) and Linder et al., Clin. Chem. 43:254-266 (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing PCa.

In one embodiment, a physician or clinician may consider applying knowledge obtained in relevant pharmacogenomics studies, e.g., using a method described herein, when determining whether to administer a pharmaceutical composition, e.g., an anticancer agent or a combination of anticancer agents, to a subject. In another embodiment, a physician or clinician may consider applying such knowledge when determining the dosage, e.g., amount per treatment or frequency of treatments, of a treatment, e.g., an anticancer agent or combination of anticancer agents, administered to a patient.

As one example, a physician or clinician may determine (or have determined, e.g., by a laboratory) the genetic profile of a subject as described herein, and optionally one or more other markers associated with PCa, of one or a group of subjects who may be participating in a prostate cancer clinical trial designed to test the efficacy of a pharmaceutical composition, e.g., an anticancer agent or combination of anticancer agents, and wherein the physician or clinician attempts to correlate the genotypes of the subjects with their response to the pharmaceutical composition.

As another example, information regarding a genetic profile associated with an increased risk of PCa, as described herein, can be used to stratify or select a subject population for a clinical trial. The information can, in some embodiments, be used to stratify individuals that may exhibit a toxic response to a treatment from those that will not. In other cases, the information can be used to separate those that will be non-responders from those who will be responders. The genetic profiles described herein can be used in pharmacogenomics-based design and manage the conduct of a clinical trial, e.g., as described in U.S. Pat. Pub. No. 2003/0108938.

As another example, information regarding a genetic profile associated with an increased risk of PCa, as described herein, can be used to stratify or select human cells or cell lines for drug testing purposes. Human cells are useful for studying the effect of a polymorphism on physiological function, and for identifying and/or evaluating potential therapeutic agents for the treatment of PCa, e.g., chemotherapeutic agents. Thus the methods can include performing the present methods on genetic material from a cell line.

Theranostics

Also included herein are compositions and methods for the identification and treatment of subjects who have an increased risk of PCa, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to PCa, the methods and compositions described herein also provide a means of optimizing the treatment of a subject having such a disorder. Provided herein is a theranostic approach to treating and preventing PCa, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a genetic profile as described herein and any measurable or quantifiable parameter relating to the outcome of the treatment, e.g., efficacy (the results of which may be binary (i.e., yes and no) as well as along a continuum), side-effect profile, recurrence, metastasis, hospitalizations, total healthcare cost, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, low recurrence, low metastasis, low total healthcare cost, and/or acceptable dose response curves) and a selected genetic profile can influence treatment such that the treatment is recommended or selected for a subject having the selected genetic profile.

Kits

Also within the scope of the invention are kits comprising a probe that hybridizes with a region of human chromosome as described herein and can be used to detect a polymorphism described herein, e.g., for use in a method described herein. The kit can include one or more other elements including: instructions for use; and other reagents, e.g., a label, or an agent useful for attaching a label to the probe. Instructions for use can include instructions for diagnostic applications of the probe for assessing risk of PCa in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to and detect other genetic variants associated with risk for PCa, e.g., as known in the art and described herein. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to PCa as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular genetic profile and the information regarding the subject, e.g., to detect correlations between a genetic profile and a particular endophenotype, or treatment response.

Engineered Cells

Also provided herein are engineered cells that harbor one or more polymorphisms described herein, e.g., one or more polymorphisms that constitute a genetic profile associated with PCa. Such cells are useful for studying the effect of a polymorphism on physiological function, and for identifying and/or evaluating potential therapeutic agents for the treatment of PCa, e.g., anti-cancer agents.

As one example, includes cells harboring one or more of the variant angiogenesis-associated alleles described herein Methods are known in the art for generating cells possessing altered sequence variants, such as homologous recombination between the endogenous gene and exogenous DNA molecule that is introduced into a cell (e.g., a cell of an animal). In some embodiments, the cells can be used to generate transgenic animals using well established methods.

The cells are preferably mammalian cells, e.g., neuronal type cells, in which an endogenous gene has been altered to include a polymorphism as described herein. Techniques such as targeted homologous recombination, can be used to insert the heterologous DNA, e.g., as described in Chappel, U.S. Pat. No. 5,272,071; and WO 91/06667.

EXAMPLES

The invention is further described in the following examples, which do not limit the scope of the invention described in the claims.

Example 1. Chemokine SNPS in Men of African Descent

Genetic alterations and altered expression of chemokines and their receptors have been linked to the susceptibility, development and survival of numerous cancers, including prostate cancer [8-15]. In fact, over expression of CCL5 and CCR5 have been detected in prostate tissue and associated with aggressive disease, presumably by triggering leukocyte production and promoting cell survival, proliferation, invasion and metastasis [13,16-18]. Coding and regulatory regions of a number of chemokine-associated genes directly influence chemokine production and have been demonstrated to modulate the risk of developing various cancers [19,20]. The CCL5-403A allele confers an increased risk of prostate, oral and pancreatic cancer [21-23]. Furthermore, inheritance of the CCR7 rs3136685 AG+AA or CCR7 rs3136687 (AG, AG+AA) genotypes was associated with a 60-62% reduction in multiple myeloma (MM) and chronic lymphocytic leukemia, respectively [24,25]. These previously mentioned studies focused on single SNPs in relation to cancer primarily among men of European descent. Consequently, the influence of individual CCL5, CCR5, CCR7 and other chemokine associated sequence variants or their combined effects on PCA was previously unknown among men of African descent.

Thus, the current study systematically evaluated main effects and synergistic interactions among 43 chemokine-related sequence variants in relation to prostate cancer susceptibility among men of African Descent from the U.S. and Jamaica. Emphasis was placed on complex interactions among highly variant apoptosis-related polymorphisms that remain under-reported in current PCA epidemiology studies. These interactions were analyzed using a well-integrated statistical approach, involving logistic regression analysis, multi-factor dimensionality reduction (MDR) modeling, and information gain theory. MDR is a rigorous statistical tool designed, in part, to evaluate main effects and complex interactions in relationship to a discrete outcome. Information gain (IG) theory indicates whether significant interactions identified from MDR are redundant or synergistic, and whether a combination of markers have a greater capacity to predict risk relative to any target when considered alone.

Study Population

The current study consisted of 279 cases and 535 controls obtained from two independent case control study sets, as summarized in Table 1-3. These studies include the Prostate Cancer Clinical Outcome Study (PC2OS) at the University of Louisville and the Prostate Cancer Study in Jamaica, University of the West Indies, Mona Campus. For the PC2OS study, 603 unrelated male residents were recruited from the Washington, D.C. and Columbia, S.C. areas through the Howard University Hospital (HUH) Division of Urology or related PCA screening programs between 2001 and 2005. This population of men of African descent (i.e., self-reported African Americans, East African Americans, West African Americans, and Afro-Caribbean Americans) consisted of 170 incident PCA cases and 433 controls (Table 2). Between March 2005 and July 2007, two hundred twenty-one unrelated Jamaican men were recruited and consecutively enrolled into the prostate cancer case-control study (109 prostate cancer cases, 102 controls) during their first time visit at urology clinics (Table 3). Details on case and control ascertainment and inclusion criteria for both sub-populations have ben detailed elsewhere [26,27].

TABLE 1

Baseline Characteristics among men of African Descent from the US & Jamaica

| Characteristics | Cases | Controls | p value[a] |
|---|---|---|---|
| Number of Participants, n | 279 | 535 | — |
| Age at enrollment (yrs), Median (range) | 67 (45-91) | 53 (27-89) | <0.0001 |
| Family History of Prostate Cancer, n (%) | | | |
| Yes | 35 (16.1) | 21 (12.5) | 0.316 |
| No | 182 (83.9) | 147 (87.5) | |
| Missing | 62 (22.2) | 367 (68.6) | |
| PSA (ng/ml), median | 11.7 (0.01-10,000) | 0.9 (0.0-4.0) | <0.0001 |
| PSA (ng/ml),[b] n (%) | | | |
| <4 | 37 (13.8) | 517 (99.8) | <0.0001 |
| ≥4 | 231 (86.2) | 1 (0.2) | |
| Missing | 11 (0.04) | 17 (0.03) | |
| Gleason Score,[b] n (%) | | | |
| 4 | 12 (5.6) | | |
| 5 | 14 (6.5) | | |
| 6 | 74 (34.2) | | |
| 7 | 70 (32.4) | | |
| 8 | 18 (8.3) | | |
| 9 | 22 (10.2) | | |
| 10 | 6 (2.8) | | |
| Missing | 63 (22.6) | | |
| Global WAA, mean (SD) | 0.79 (0.25-0.94) | 0.767 (0.25-0.95) | 0.107 |

Abbreviations:
PSA, prostate specific antigen;
WAA, West African Ancestry;
[a]Differences in frequencies were tested by a Chi-square test of heterogeneity; differences in median age (yrs) and Global West African Ancestry between cases and controls were tested using the Wilcoxon sum Rank test

TABLE 2

Baseline Characteristics among men of African Descent from the US

| Characteristics | Cases | Controls | p value[a] |
|---|---|---|---|
| Number of Participants, n | 170 | 433 | — |
| Age at diagnosis (yrs), Median (range) | 65 (45-91) | 51 (27-89) | <0.0001 |
| Family History of Prostate Cancer, n (%) | | | |
| Yes | 18 (16.7) | 9 (13.6) | 0.592 |
| No | 90 (83.3) | 57 (86.4) | |
| Missing | 62 (36.5) | 367 (84.8) | |
| PSA (ng/ml), median (range) | 7.0 (0.01-5,000) | 0.9 (0.0-3.9) | <0.0001 |
| PSA (ng/ml), n (%) | | | |
| <4 | 37 (23.1) | 416 (100.0) | <0.0001 |
| ≥4 | 123 (76.9) | 0 (0.0) | |
| Missing | 10 (5.9) | 17 (1.6) | |
| Gleason Score,[b] n (%) | | | |
| 4 | 12 (11.1) | | |
| 5 | 14 (13.0) | | |

TABLE 2-continued

Baseline Characteristics among men of African Descent from the US

| Characteristics | Cases | Controls | p value[a] |
|---|---|---|---|
| 6 | 29 (26.9) | | |
| 7 | 32 (29.6) | | |
| 8 | 5 (4.6) | | |
| 9 | 12 (11.1) | | |
| 10 | 4 (3.7) | | |
| Missing | 62 (36.5) | | |
| Global WAA, mean (SD) | 0.79 (0.25-0.94) | 0.77 (0.25-0.94) | 0.107 |

Abbreviations:

PSA, prostate specific antigen;

[a]Differences in frequencies were tested by a Chi-square test of heterogeneity or Fisher's Exact Test; differences in median age (yrs) between cases and controls were tested using the Wilcoxon sum Rank test.

TABLE 3

Baseline Characteristics among men from Jamaica

| Characteristics | Cases | Controls | p value[a] |
|---|---|---|---|
| Number of Participants, n | 109 | 102 | — |
| Age at diagnosis (yrs), Median (range) | 70 (49-80) | 60 (40-80) | <0.0001 |
| Family History of Prostate Cancer, n (%) | | | |
| Yes | 17 (15.6) | 12 (11.8) | 0.272 |
| No | 92 (84.4) | 90 (88.2) | |
| Missing | 0 (0.0) | 0 (0.0) | |
| PSA (ng/ml), median (range) | 35.0 (4.0-10,000) | 1.2 (0.2-4.0) | <0.0001 |
| PSA (ng/ml), n (%) | | | |
| <4 | 0 (0.0) | 101 (99.0) | <0.0001 |
| ≥4 | 108 (100.0) | 1 (1.0) | |
| Missing | 0 (0.0) | 0 (0.0) | |
| Gleason Score,[b] n (%) | | | |
| 4 | — | | |
| 5 | — | | |
| 6 | 45 (41.7) | | |
| 7 | 38 (35.2) | | |
| 8 | 13 (12.0) | | |
| 9 | 10 (9.3) | | |

TABLE 3-continued

Baseline Characteristics among men from Jamaica

| Characteristics | Cases | Controls | p value[a] |
|---|---|---|---|
| 10 | 2 (1.8) | | |
| Missing | 1 (0.01) | | |

Abbreviations:

PSA, prostate specific antigen;

[a]Differences in frequencies were tested by a Chi-square test of heterogeneity or Fisher's Exact Test; differences in median age (yrs) between cases and controls were tested using the Wilcoxon sum Rank test.

Men diagnosed with prostate cancer were 10-14 years older and had higher PSA levels than controls (P<0.0001). Disease-free men from Jamaica were about 9 years older than US controls; however, there were no significant differences in family history of prostate cancer or PSA levels. Jamaican cases had 7 fold higher PSA levels (P<0.0001) and slightly higher median Gleason scores (P=0.018) compared to cases from the US. There were no differences in the distribution of family history of prostate cancer comparing: (1) cases to controls from the total population (P=0.316) (Table 5), US alone (P=0.592) (Table 6), or Jamaica alone (P=0.272) (Table 3), and (2) controls (P=0.757) or cases (P=0.830) comparing the two study centers.

Criteria for Chemokine and Chemokine Receptor Gene and SNP Selection

Chemokine-associated genes and SNPs were selected using one or more of following criteria: (1) epidemiological or molecular biological evidence from published reports indicating a relationship between the SNP/gene with cancer or inflammatory/immune response related diseases; (2) commonly studied loci; (3) marked disparities in genotype frequency comparing men of African descent to their Caucasian counterparts (i.e., ±10% change); (4) evidence demonstrating a link with alterations in mRNA expression/stability or protein expression/structure or function using in silico tools (e.g., SNPinfo) or published reports (Xu and Taylor, (2009) Nucl. Acids Res. 37(Supp2):W600-W605; snpinfo.niehs.nih.gov/snpfunc.htm); and (5) a minor allele frequency ≥1% reported in the National Center for Biotechnology Information (NCBI) Entrez SNP, (ncbi.nlm.nih.gov, dbSNP build 136). On average, a majority of the SNPs had minor allele frequencies ranging from 26-27%. However, five SNPs with allele frequencies greater than 1% but less than 5% were included in the analysis to explore whether rare SNPs would lead to substantial gains in effect sizes (i.e., 2-3 fold increases in risk) and contribute to missing genetic heritability [28,29]. The SNPinfo webserver enabled us to annotate and/or predict the functional consequence of chemokine-associated sequence variants on alternative alleles, as summarized in Table 4.

TABLE 4

Functional Consequence of Chemokine-Associated Sequence Variants[a].

| dbSNP ID | Gene | Chr | Chr Position | Location | Nucleotide | Amino Acid Change | Predicted Functional Consequence |
|---|---|---|---|---|---|---|---|
| rs1012656 | CCR6 | 6 | 167445293 | UTR-5 | | | TFBS |
| rs1024611 | CCL2 | 17 | 29603901 | 5' near gene | | | TFBS |
| *rs1045879 | CXCR7 | 2 | 237154643 | Exon 1 | T > C | Leu266Leu | |
| rs11076191 | CCL17 | 16 | 55997089 | Intron 1 | | | TFBS |
| rs11574914 | CCL21 | 9 | 34700338 | 5' near gene | | | TFBS |
| rs11574915 | CCL21 | 9 | 34700084 | UTR-5 | | | TFBS, Splicing |
| rs11574916 | CCL21 | 9 | 34699239 | UTR-3 | | | TFBS, miRNA |
| rs12721497 | CCR9 | 3 | 45918134 | Exon 3 | G > A | Met284Val | nsSNP, benign |
| *rs1488371* | CCR9 | 3 | 45913093 | *Intron 2* | | | |
| rs1556413 | CCR6 | 6 | 167444733 | 5' near gene | | | TFBS |
| rs17809012 | CCL7 | 17 | 29636557 | 5' near gene | | | TFBS |
| rs17880777 | CXCL12 | 10 | 44201208 | 5' near gene | | | TFBS |
| *rs1799987* | CCR5 | 3 | 46386939 | *Intron 1* | | | *TFBS* |
| *rs1799988* | CCR5 | 3 | 46387263 | UTR-5 | | | TFBS |
| rs1800024 | CCR5 | 3 | 46387563 | Intron 2 | | | TFBS |
| rs1801157 | CXCL12 | 10 | 44188263 | UTR-3 | | | miRNA |
| rs2023305 | CCR6 | 6 | 167444888 | 5' near gene | | | TFBS |
| *rs2032887 | CCL25 | 19 | 8027360 | Exon 3 | G > A | His101Arg | Splicing, probably damaging |
| *rs2107538 | CCL5 | 17 | 31231893 | 5' near gene | | | TFBS |
| rs2227010 | CCR5 | 3 | 46386546 | 5' near gene | | | TFBS |
| rs223895 | CCL17 | 16 | 55998397 | Intron 1 | | | |
| *rs2280789 | CCL5 | 17 | 31231116 | Intron 1 | | | TFBS |
| rs2282691 | CCL1 | 17 | 29712422 | Intron 2 | | | |
| rs2286486 | CCR9 | 3 | 45902745 | 5' near gene | | | TFBS |
| rs2302004 | CCL24 | 7 | 75280791 | Intron 1 | | | TFBS |
| rs2302009 | CCL26 | 7 | 75236934 | UTR-3 | | | miRNA |
| rs266093 | CXCL12 | 10 | 44186214 | UTR-3 | | | miRNA |
| rs2812378 | CCL21 | 9 | 34700260 | 5' near gene | | | TFBS |
| rs2839685 | CXCL12 | 10 | 44201644 | 5' near gene | | | TFBS |
| rs2839695 | CXCL12 | 10 | 44193855 | UTR-3 | | | miRNA |
| rs3093023 | CCR6 | 6 | 167454280 | 5' near gene | | | |
| rs3093024 | CCR6 | 6 | 167452783 | Intron 1 | | | |
| *rs3136685* | *CCR7* | *17* | *35973325* | *Intron 1* | | | |
| rs3136687 | CCR7 | 17 | 35971422 | Intron 1 | | | |
| *rs3817655 | CCL5 | 17 | 31223754 | Intron 2 | | | TFBS |
| rs41289608 | CCR9 | 3 | 45903142 | UTR-5 | | | TFBS, Splicing |
| rs4795896 | CCL11 | 17 | 29636365 | 5' near gene | | | TFBS |
| rs523604 | CXCR5 | 11 | 118260948 | Intron 1 | | | |
| rs6550178 | CCR4 | 3 | 32968496 | Intron 1 | | | TFBS |
| rs7259568 | CCL25 | 19 | 8023608 | 5' near gene | | | TFBS |
| rs7559855 | CXCR7 | 2 | 237153189 | Intron 1 | | | |
| rs7613548 | CCR9 | 3 | 45901573 | 5' near gene | | | TFBS |
| rs7632357 | CCR4 | 3 | 32967207 | 5' near gene | | | TFBS |

Abbreviations: Chr, chromosome; UTR, untranslated region; TFBS, transcription factor binding site; miRNA, micro RNA; nsSNP, nonsynonymous SNP;
[a]Forty-three chemokine-related SNPs were analyzed among men of African Descent. SNPs denoted in bold were significantly associated with PCA risk in the total population. Italicized SNPs were significantly associated with PCA risk in the Jamaican population. Asterisked rows symbolize SNPs that were significantly associated with PCA risk in the U.S. population.

Genetic Analysis of Variant Chemokine-Associated SNPs

In order to evaluate and validate chemokine-related markers as predictors of PCA risk, de-identified germ-line DNA from PCA cases and disease-free individuals were genotyped using a custom Illumina GoldenGate Genotyping assay with VeraCode Technology and BeadXpress reader, according to the manufacturer's instructions [30].

Quality Control Assurance and Data Management of Genotype Data

At the onset of the project, allelic discrimination focused on chemokine associated SNPs among men of African Descent. To minimize misclassification bias, laboratory technicians were blinded to the case status of study participants. Each batch of up to 96 samples included four non-DNA template controls and eight duplicate samples, enabling calculation of the percent contamination and concordance rates per batch and for the entire data set, respectively. Genotype call rates were calculated separately for each SNP and study participant. Lastly, the distribution of the genotypes among disease-free individuals was tested for significant departures from the Hardy-Weinberg equilibrium (HWE).

Prior to performing marker statistics, subjects were excluded who had genotype call rates that were <90%. To ensure high quality data, nine SNPs were excluded from the final analysis if: the distribution of the genotypes among controls deviated substantially from the Hardy-Weinberg Equilibrium, using a conservative significance level cut-off value of $P \leq 0.005$ (n=1); they had a minor allele frequency <1% (n=6); or low genotype call rates <95% (n=2). Following data clean-up, 43 chemokine-related SNPs were included in the final analysis consisting of 814 men of African descent (279 cases, 535 controls). All quality control analyses and data management was performed using Golden Helix's SNP Variation Software 7.0 (Bozeman, Mont.).

Prevalence of Minor Alleles/Genotype Frequency Comparing Men of African Descent from the U.S. and Jamaica Overall, the chemokine-related SNPs were fairly common among disease-free individuals from the entire sub-population of U.S. and Jamaica, with average minor frequencies of 26-27% and a standard deviation of 14%, respectively. Thirty-eight SNPs had minor allele frequencies ≥5%. For exploratory purposes, five rare SNPs (CCR9 rs12721497, CCL17 rs11076191, CCL11 rs4795896, CCL21 rs11574916, CXCL12 rs1801157) were analyzed with minor allele frequencies ranging between 0.015-0.490. The minor allele frequency comparing controls from the US and Jamaica were strongly correlated ($R^2$=0.957). Only 5 out of the 43 SNPs analyzed were discordant comparing men of African descent from the U.S. to men from Jamaica (P<0.0487), namely CCL17 rs11076191, CCL21 rs11574916, CCR7 rs3136685, CCR7 rs3136687, and CCR9 rs12721497.

Statistical Analysis for Single Gene Effects

Univariate and multivariate analyses were used to evaluate chemokine associated SNPs among men of African descent in relation to prostate cancer risk. To assess whether inheritance of one or more chemokine allele(s) influence the risk of developing PCA, significant differences in the distribution of homozygous major, heterozygous, or homozygous minor genotypes between cases and controls were tested for using the chi-square test of heterogeneity. The association between PCA outcomes and selected polymorphic genes, expressed as odds ratios (ORs) and corresponding 95% confidence intervals (CIs), were estimated using unconditional multivariate LR models adjusted for age. LR analyses for genetic variants and PCA development were conducted using the major or common genotype as the referent category. All analyses were conducted using SAS 9.3 (SAS Institute Inc., Cary, N.C.) and SNP Variation Software 7.0 (GoldenHelix, Bozeman, Mont.). Statistical significance was assessed using a False Discovery Rate cut-off of 0.05, in order to adjust for multiple comparisons.

Statistical Power for Single Gene Effects

Calculations were conducted to determine the statistical power of our sample to detect significant relationships between chemokine and chemokine-related genotypes and PCA development. The expected risk estimates of the study can be estimated by specifying values for a number of parameters, including a minor allele frequency of at least 26.5%, National Cancer Institute's estimate of PCA disease prevalence (19%), number of cases (n=279), and number of controls (n=535). The causal SNP was assumed to be in complete linkage disequilibrium with predisposing variant ($r^2$=1.0). Based on the sample size for the total population, U.S. and Jamaican men, the study has >80% power to detect genetic markers with odds ratios (ORs) of ≥1.5, ≥1.55, and ≥2.0 for PCA risk, respectively, for minor allele frequency of at least 26.5%, assuming a co-dominant genetic model with 1 degree of freedom (df). Power calculations were performed using Power for Genetic Association Version 2 Software [31].

Relationship Between Chemokine Sequence Variants and Prostate Cancer Risk

Among all men of African descent, five sequence variants were significantly associated with the risk of developing prostate cancer, as summarized in Table 5. Possession of the CCL5 rs2107538 AA ($OR_{unadjusted}$=0.52; 95% CI=0.34, 0.80) or CCL5 rs3817655 TA+AA ($OR_{unadjusted}$=0.54; 95% CI=0.40, 0.74) genotype was linked with a 41-48% reduction in PCA risk in the unadjusted LR models. These effects remained significant for both SNPs after adjusting for age (CCL5 rs3817655: $OR_{adjusted}$=0.56; 95% CI=0.39, 0.81 and CCL5 rs2107538: $OR_{adjusted}$=0.66; 95% CI=0.46, 0.96). The recessive genetic model for CCR5 rs1799988 ($OR_{adjusted}$=1.52; 95% CI=1.02, 2.26) as well as the dominant models for CCR7 rs3136685 ($OR_{adjusted}$=1.66; 95% CI=1.09, 2.54) and CCR7 rs3136687 ($OR_{adjusted}$=1.14; 95% CI=1.12, 1.16), respectively, were associated with a significant 1.14-1.66 fold increase in PCA risk within the age adjusted LR models. After controlling for multiple comparisons, the dominant genetic models for the two CCL5 SNPs (rs2107538, rs3817655) remained significant with false-discovery rates (FDR) ≤0.0150, whereas the recessive model for CCR5 rs1799988 was marginally significant (FDR=0.0494).

TABLE 5

Association between Chemokine Associated SNPs and Prostate Cancer Risk Among men of African Descent.

| Genes | dbSNP ID | Location Predicted Function† | Genotype | Cases n (%) | Controls n (%) | Unadjusted OR (95% CI) | Adjusted OR (95% CI) | P-value | P-trend | FDR |
|---|---|---|---|---|---|---|---|---|---|---|
| CCR5 | rs1799988 | 5'UTR TFBS | TT | 85 (30.7) | 194 (36.7) | 1.00 (referent) | 1.00 (referent) | 0.005 | 0.0039 | 0.0682 |
| | | | TC | 107 (38.6) | 227 (43.9) | 1.08 (0.76, 1.52) | 0.83 (0.55, 1.25) | 0.676 | | |
| | | | CC | ??? | 108 (20.4) | 1.80 (1.23, 2.63) | 1.38 (0.87, 2.17) | 0.003 | | |
| | | | TC + CC | 192 (69.3) | 335 (63.3) | 1.31 (0.96, 1.78) | 1.01 (0.70, 1.46) | 0.090 | | 0.4823 |
| | | | CC vs (TT + TC) | | | 1.73 (1.24, 2.40) | 1.52 (1.02, 2.26) | 0.0013 | | 0.0494 |
| CCL5 | rs2107538 | 5' near gene TFBS | GG | 111 (39.8) | 150 (28.1) | 1.00 (referent) | 1.00 (referent) | 0.002 | 0.001 | 0.0493 |
| | | | GA | 124 (44.4) | 270 (50.6) | 0.62 (0.45, 0.86) | 0.72 (0.49, 1.06) | 0.004 | | |
| | | | AA | 44 (15.8) | 114 (21.4) | 0.52 (0.34, 0.80) | 0.53 (0.32, 0.89) | 0.003 | | |
| | | | GA + AA | 168 (60.2) | 384 (71.9) | 0.59 (0.44, 0.80) | 0.66 (0.46, 0.96) | 0.0007 | | 0.0150 |
| | | | AA vs (GG + GA) | | | 0.83 (0.57, 1.20) | 0.74 (0.47, 1.16) | 0.057 | | 0.4735 |
| CCL5 | rs3817655 | Intron 2 TFBS | TT | 114 (41.0) | 147 (27.5) | 1.00 (referent) | 1.00 (referent) | 0.004 | 0.002 | 0.019 |
| | | | TA | 115 (41.4) | 278 (52.0) | 0.53 (0.38, 0.74) | 0.57 (0.38, 0.84) | 0.0002 | | |
| | | | AA | 49 (17.6) | 110 (20.5) | 0.57 (0.38, 0.87) | 0.54 (0.32, 0.89) | 0.0009 | | |
| | | | TA + AA | 164 (59.0) | 388 (72.5) | 0.54 (0.40, 0.74) | 0.56 (0.39, 0.81) | 0.0001 | | 0.0038 |
| | | | AA vs (TT + TA) | | | 0.83 (0.57, 1.20) | 0.74 (0.47, 1.16) | 0.317 | | 1.0000 |
| CCR7 | rs3136685 | Intron 1 | TT | 55 (19.7) | 151 (28.3) | 1.00 (referent) | 1.00 (referent) | 0.029 | 0.031 | 0.3078 |
| | | | TC | 139 (49.8) | 237 (44.4) | 1.61 (1.11, 2.34) | 1.86 (1.18, 2.92) | 0.012 | | |

TABLE 5-continued

Association between Chemokine Associated SNPs and Prostate Cancer Risk Among men of African Descent.

| Genes | dbSNP ID | Location Predicted Function† | Genotype | Cases n (%) | Controls n (%) | Unadjusted OR (95% CI) | Adjusted OR (95% CI) | P-value | P-trend | FDR |
|---|---|---|---|---|---|---|---|---|---|---|
| | | | CC | 85 (30.5) | 146 (27.3) | 1.60 (1.06, 2.40) | 1.39 (0.85, 2.28) | 0.024 | | |
| | | | TC + CC | 224 (80.3) | 383 (71.7) | 1.61 (1.13, 2.28) | 1.66 (1.09, 2.54) | 0.008 | | 0.5990 |
| | | | CC vs (TT + TC) | | | 1.16 (0.85, 1.60) | 0.92 (0.62, 1.35) | 0.348 | | 0.1615 |
| CCR7 | rs3136687 | Intron 1 | TT | 84 (30.1) | 173 (32.4) | 1.00 (referent) | 1.00 (referent) | 0.041 | 0.458 | 0.3523 |
| | | | TC | 153 (54.8) | 249 (46.5) | 1.26 (0.91, 1.76) | 1.45 (0.97, 2.16) | 0.161 | | |
| | | | CC | 42 (15.1) | 113 (21.1) | 0.77 (0.49, 1.19) | 0.96 (0.57, 1.62) | 0.234 | | |
| | | | TC + CC | 195 (69.9) | 362 (67.6) | 1.11 (0.81, 1.52) | 1.14 (1.12, 1.16) | 0.516 | | 0.7159 |
| | | | CC vs (TT + TC) | | | 0.66 (0.45, 0.98) | 0.76 (0.49, 1.20) | 0.037 | | 0.5092 |

In an exploratory analysis, risk estimates were evaluated for all 43 chemokine targets for each racial/ethnic group, as depicted in Table 6. Among U.S. men, CXCR7 rs1045879, CCL25 rs2032887, CCL5 rs2107538, and CCL5 rs3817655 were associated with PCA risk. Inheritance of the CCL25 rs2032887 AG+GG ($OR_{unadjusted}$=0.66; 95% CI=0.46, 0.96), CCL5 rs2107538 GA+AA ($OR_{unadjusted}$=0.52; 95% CI=0.36, 0.76), CCL5 rs2280789 AG ($OR_{unadjusted}$=0.60; 95% CI=0.40, 0.90), and CCL5 rs3817655 TA+AA ($OR_{unadjusted}$=0.46; 95% CI=0.32, 0.68) genotypes were significantly associated with a 34-54% reduction in the risk of developing PCA with chi-square p-values ranging from 0.0001-0.027. Although the magnitude of the reduction in PCA risk for CCL25 rs2032887 AG+GG ($OR_{unadjusted}$=0.66, $OR_{adjusted}$=0.68) and CCL5 rs3817655 TA+AA ($OR_{unadjusted}$=0.46, $OR_{adjusted}$=0.51) genotypes remained practically unchanged after adjusting for age, the findings only remained significant for CCL5 rs33817655 SNP after the adjustment. The 1.5 fold increase in PCA susceptibility linked with the CXCR2 rs1045879 AG+GG genotype ($OR_{unadjusted}$=1.54; 95% CI=1.07, 2.22; P=0.02) was lost in the age adjusted risk models.

In the Jamaican population, there was a two-fold increase in PCA susceptibility associated with CCR5 rs1799987 AA ($OR_{unadjusted}$=2.18; 95% CI=1.04, 4.58), CCR5 rs1799988 recessive ($OR_{unadjusted}$=1.96; 95% CI=1.04, 3.70), and CCR7 rs3136685 TC+CC($OR_{unadjusted}$=2.3; 95% CI=1.05, 5.07) genotypes, with corresponding chi-square P-values ranging from 0.02-0.037. Additionally, a 40% reduction in PCA risk was observed for individuals who possessed the CCR9 rs1488371 CA+AA genotype ($OR_{unadjusted}$=0.46; 95% CI=0.23, 0.94). Out of the 4 markers, the CCR7 rs3136685 SNP remained significant after adjusting for age alone or age combined with family history. Notably, the magnitude of PCA risk estimates did not change for the CCR5, CCL5, and CCR9 SNPs, comparing the adjusted unadjusted risk models.

TABLE 6

Association between Chemokine Associated SNPs and Prostate Cancer Risk, Stratified by Racial Ethnic Group.

| Genes | dbSNP ID | Location Predicted Function | Genotype | Unadjusted OR (95% CI) US Men | Unadjusted OR (95% CI) Jamaican Men | Age-Adjusted OR (95% CI) US Men | Age-Adjusted OR (95% CI) Jamaican Men | p-value US Men | p trend US Men | p-value Jamaican Men | p trend Jamaican Men |
|---|---|---|---|---|---|---|---|---|---|---|---|
| CCR5 | rs1799988 | 5'UTR | TT | 1.00 (referent) | 1.00 (referent) | 1.00 (referent) | 1.00 (referent) | 0.063 | 0.076 | 0.085 | 0.034 |
| | | TFBS | TC | 0.95 (0.62, 1.44) | 1.26 (0.66, 2.40) | 0.68 (0.42, 1.12) | 1.23 (0.60, 2.52) | 0.808 | | 0.484 | |
| | | | CC | 1.58 (0.99, 2.49) | 2.25 (1.08, 4.71) | 1.06 (0.60, 1.85) | 2.23 (0.99, 5.00) | 0.053 | | 0.031 | |
| | | | TC + CC | 1.15 (0.79, 1.68) | 1.56 (0.86, 2.82) | 0.80 (0.52, 1.26) | 1.55 (0.81, 2.98) | 0.453 | | 0.142 | |
| | | | CC vs (TT + TC) | 1.62 (1.08, 2.42) | 1.96 (1.04, 3.70) | 1.28 (0.78, 2.12) | 1.98 (0.98, 3.98) | 0.020 | | 0.037 | |
| CCL5 | rs2107538 | 5' near gene | GG | 1.00 (referent) | 1.00 (referent) | 1.00 (referent) | 1.00 (referent) | 0.003 | 0.002 | 0.286 | 0.116 |
| | | TFBS | GA | 0.54 (0.36, 0.80) | 0.75 (0.40, 1.40) | 0.67 (0.42, 1.08) | 0.82 (0.40, 1.64) | 0.003 | | 0.375 | |
| | | | AA | 0.48 (0.28, 0.82) | 0.53 (0.24, 1.16) | 0.53 (0.28, 1.01) | 0.52 (0.22, 1.22) | 0.007 | | 0.116 | |
| | | | GA + AA | 0.52 (0.36, 0.76) | 0.68 (0.38, 1.23) | 0.63 (0.40, 0.99) | 0.72 (0.37, 1.40) | 0.001 | | 0.204 | |
| | | | AA vs (GG + GA) | 0.68 (0.42, 1.11) | 0.64 (0.32, 1.26) | 0.66 (0.37, 1.20) | 0.58 (0.28, 1.24) | 0.125 | | 0.192 | |
| CCL5 | rs2280789 | Intron 1 | AA | 1.00 (referent) | 1.00 (referent) | 1.00 (referent) | 1.00 (referent) | 0.039 | 0.018 | 0.508 | 0.823 |

TABLE 6-continued

Association between Chemokine Associated SNPs and Prostate Cancer Risk, Stratified by Racial Ethnic Group.

| Genes | dbSNP ID | Location Predicted Function | Genotype | Unadjusted OR (95% CI) US Men | Unadjusted OR (95% CI) Jamaican Men | Age-Adjusted OR (95% CI) US Men | Age-Adjusted OR (95% CI) Jamaican Men | p-value US Men | p trend US Men | p-value Jamaican Men | p trend Jamaican Men |
|---|---|---|---|---|---|---|---|---|---|---|---|
| | | TFBS | AG | 0.60 (0.40, 0.90) | 1.20 (0.66, 2.18) | 0.60 (0.37, 0.97) | 1.48 (0.76, 2.89) | 0.015 | | 0.549 | |
| | | | GG | 0.62 (0.24, 1.56) | 0.59 (0.18, 1.89) | 1.00 (0.34, 2.99) | 0.42 (0.12, 1.46) | 0.309 | | 0.373 | |
| | | | AG + GG | 0.60 (0.41, 0.89) | 1.06 (0.61, 1.86) | 0.64 (0.40, 1.01) | 1.18 (0.63, 2.20) | 0.011 | | 0.820 | |
| | | | GG vs (AA + AG) | 0.72 (0.28, 1.82) | 0.55 (0.18, 1.80) | 1.14 (1.12, 1.18) | 0.36 (0.10, 1.27) | 0.488 | | 0.313 | |
| CCL5 | rs3817655 | Intron 2 | TT | 1.00 (referent) | 1.00 (referent) | 1.00 (referent) | 1.00 (referent) | 0.000 | 0.003 | 0.275 | 0.110 |
| | | TFBS | TA | 0.44 (0.29, 0.65) | 0.72 (0.38, 1.34) | 0.49 (0.30, 0.80) | 0.74 (0.36, 1.50) | <0.0001 | | 0.302 | |
| | | | AA | 0.56 (0.34, 0.92) | 0.53 (0.24, 1.16) | 0.54 (0.29, 1.02) | 0.50 (0.22, 1.20) | 0.022 | | 0.115 | |
| | | | TA + AA | 0.46 (0.32, 0.68) | 0.66 (0.36, 1.20) | 0.51 (0.32, 0.80) | 0.66 (0.34, 1.28) | <0.0001 | | 0.167 | |
| | | | AA vs (TT + TA) | 0.88 (0.55, 1.40) | 0.66 (0.34, 1.28) | 0.80 (0.46, 1.42) | 0.61 (0.28, 1.27) | 0.577 | | 0.220 | |
| CCL25 | rs2032887 | Exon 3 | AA | 1.00 (referent) | 1.00 (referent) | 1.00 (referent) | 1.00 (referent) | 0.084 | 0.034 | 0.474 | 0.379 |
| | | ESE or ESS nsSNP | AG | 0.67 (0.46, 0.99) | 1.42 (0.80, 2.48) | 0.70 (0.44, 1.11) | 1.54 (0.82, 2.88) | 0.404 | | 0.225 | |
| | | | GG | 0.61 (0.29, 1.28) | 1.10 (0.36, 3.38) | 0.57 (0.22, 1.42) | 0.84 (0.24, 2.88) | 0.196 | | 0.860 | |
| | probably | | AG + GG | 0.66, (0.46, 0.96) | 1.37 (0.80, 2.36) | 0.68 (0.44, 1.05) | 1.42 (0.78, 2.60) | 0.027 | | 0.253 | |
| | damaging missense R > H | | GG vs (AA + AG) | 0.71 (0.34, 1.47) | 0.93 (0.32, 2.75) | 0.65 (0.26, 1.60) | 0.68 (0.20, 2.24) | 0.357 | | 0.898 | |
| CCR5 | rs1799987 | Intron 1 | GG | 1.00 (referent) | 1.00 (referent) | 1.00 (referent) | 1.00 (referent) | 0.197 | 0.951 | 0.107 | 0.041 |
| | | | GA | 1.29 (0.88, 1.92) | 1.28 (0.68, 2.44) | 0.89 (0.56, 1.44) | 1.25 (0.61, 2.56) | 0.191 | | 0.442 | |
| | | TFBS | AA | 0.84 (0.48, 1.48) | 2.18 (1.04, 4.58) | 0.58 (0.29, 1.14) | 2.20 (0.98, 4.94) | 0.558 | | 0.039 | |
| | | | GA + AA | 1.18 (0.80, 1.70) | 1.56 (0.86, 2.82) | 0.81 (0.52, 1.26) | 1.55 (0.81, 2.98) | 0.399 | | 0.142 | |
| | | | AA vs (GG + GA) | 0.72 (0.44, 1.21) | 1.88 (0.99, 3.56) | 0.61 (0.32, 1.15) | 1.92 (0.96, 3.88) | 0.222 | | 0.051 | |
| CCR7 | rs3136685 | Intron 1 | TT | 1.00 (referent) | 1.00 (referent) | 1.00 (referent) | 1.00 (referent) | 0.381 | 0.731 | 0.103 | 0.086 |
| | | | TC | 1.32 (0.86, 2.02) | 2.24 (0.98, 5.16) | 1.58 (0.94, 2.66) | 2.78 (1.09, 7.08) | 0.197 | | 0.056 | |
| | | | CC | 1.07 (0.65, 1.76) | 2.38 (1.02, 5.58) | 1.02 (0.56, 1.86) | 2.52 (0.97, 6.52) | 0.778 | | 0.045 | |
| | | | TC + CC | 1.23 (0.82, 1.84) | 2.3 (1.05, 5.07) | 1.36 (0.83, 2.21) | 2.66 (1.10, 6.42) | 0.305 | | 0.037 | |
| | | | CC vs (TT + TC) | 0.90 (0.59, 1.36) | 1.28 (0.74, 2.25) | 0.76 (0.46, 1.26) | 1.16 (0.62, 2.15) | 0.622 | | 0.372 | |
| CCR7 | rs3136687 | Intron 1 | TT | 1.00 (referent) | 1.00 (referent) | 1.00 (referent) | 1.00 (referent) | 0.022 | 0.294 | 0.229 | 0.218 |
| | | | TC | 1.42 (0.89, 2.24) | 2.16 (0.84, 5.56) | 1.47 (0.85, 2.54) | 1.52 (0.53, 4.38) | 0.133 | | 0.110 | |
| | | | CC | 0.78 (0.46, 1.34) | 2.20 (0.84, 5.69) | 0.85 (0.45, 1.59) | 1.34 (0.46, 3.96) | 0.380 | | 0.106 | |
| | | | TC + CC | 1.17 (0.76, 1.81) | 2.18 (0.88, 5.38) | 1.22 (0.72, 2.05) | 1.44 (0.52, 3.98) | 0.482 | | 0.092 | |
| | | | CC vs (TT + TC) | 0.61 (0.40, 0.93) | 1.17 (0.68, 2.02) | 1.14 (1.12, 1.18) | 0.94 (0.51, 1.75) | 0.023 | | 0.573 | |
| CCR9 | rs1488371 | Intron 2 | CC | 1.00 (referent) | 1.00 (referent) | 1.00 (referent) | 1.00 (referent) | 0.013 | 0.902 | 0.003 | 0.018 |
| | | | CA | 0.94 (0.62, 1.40) | 0.52 (0.26, 1.08) | 0.88 (0.54, 1.42) | 0.60 (0.26, 1.31) | 0.747 | | 0.080 | |
| | | | AA | 1.57 (0.50, 4.90) | — | 0.92 (0.22, 3.80) | — | 0.435 | | 0.984 | |
| | | | CA + AA | 0.98 (0.66, 1.44) | 0.46 (0.23, 0.94) | 0.88 (0.54, 1.40) | 0.48 (0.22, 1.04) | 0.901 | | 0.034 | |
| | | | AA vs (AA + CA) | 1.60 (0.52, 4.97) | — | 0.95 (0.23, 4.00) | — | 0.414 | | 0.984 | |

TABLE 6-continued

Association between Chemokine Associated SNPs and Prostate Cancer Risk, Stratified by Racial Ethnic Group.

| Genes | dbSNP ID | Location Predicted Function | Genotype | Unadjusted OR (95% CI) US Men | Unadjusted OR (95% CI) Jamaican Men | Age-Adjusted OR (95% CI) US Men | Age-Adjusted OR (95% CI) Jamaican Men | p-value US Men | p trend US Men | p-value Jamaican Men | p trend Jamaican Men |
|---|---|---|---|---|---|---|---|---|---|---|---|
| CXCR7 | rs1045879 | Exon 1 | AA | 1.00 (referent) | 1.00 (referent) | 1.00 (referent) | 1.00 (referent) | 0.065 | 0.038 | 0.459 | 0.762 |
| | | synSNP | AG | 1.54 (1.06, 2.26) | 1.38 (0.77, 2.48) | 1.30 (0.82, 2.04) | 1.30 (0.68, 2.50) | 0.025 | | 0.279 | |
| | | L > L | GG | 1.53 (0.84, 2.79) | 0.86 (0.34, 2.16) | 1.02 (0.47, 2.20) | 0.74 (0.27, 2.04) | 0.166 | | 0.756 | |
| | | | AG + GG | 1.54 (1.07, 2.22) | 1.24 (0.72, 2.14) | 1.24 (0.80, 1.93) | 1.15 (0.62, 2.10) | 0.020 | | 0.431 | |
| | | | GG vs (AA + AG) | 1.21 (0.69, 2.13) | 0.76 (0.31, 1.84) | 0.88 (0.42, 1.84) | 0.67 (0.25, 1.80) | 0.499 | | 0.538 | |

Abbreviations: UTR, untranscription region; TFBS, transcription factor binding site; ESE, exonic splicing enhancers; ESS, exonic splicing silencers; nsSNP, non-synonymous coding SNP; synSNP, synonymous SNP Analysis of Gene Interactions Using Multi-Factor Dimensionality Reduction (MDR)

To evaluate the single- and joint-modifying effects of 43 candidate chemokine-associated SNPs within a large dataset is computationally challenging [32,33]. In order to overcome this problem, open source and freely available MDR 2.0 was used to detect and characterize all possible one-, two-, and three-way interaction models in relation to PCA (SourceForge, Inc) [34]. To reduce computation time needed to process millions of SNP combinations in relation to prostate cancer risk, MDR was distributed on a workstation with 12 hyper-threaded cores across two central processing units (total of 24 simultaneous threads of execution) and 24 GB of RAM. Although MDR has been described elsewhere, for convenience we provide a brief summary. This method is able to detect and characterize high-order interactions in case-control studies, and remains effective with relatively small sample sizes (i.e., ≥200 cases and ≥200 controls) [35]. MDR has excellent statistical power (>80%) to identify gene-gene interactions even in the presence of 5% genotyping error and/or 5% missing data. With MDR, multi-locus genotypes are pooled into high-risk and low-risk groups, reducing high-dimensional data to a single variable dimension and permitting an investigation of gene-gene interactions. This one-dimensional multi-locus genotype variable is then evaluated for its ability to classify and predict a disease outcome through cross-validation and permutation testing. Finally, among all of the gene-gene combinations, a single model is selected that maximizes the case-to-control ratio of the high-risk groups while minimizing classification and prediction errors. MDR uses a 10-fold cross validation to estimate the testing accuracy of a model and provide measure of overfitting. The model is developed on 9/10 of the data and then evaluated on the remaining test set. This process is repeated for each 1/10 of the data and the resulting prediction accuracies are averaged. In the current study, the model with the greatest cross validation consistency (CVC) [i.e., ≥8/10] and highest Average Testing Accuracy (ATA) was selected as the best predictor of disease outcome [36,37]. MDR models are validated by comparing the average CVC to the distribution of the average consistencies under the null hypothesis of no association, derived empirically from 1,000 permutations. The null hypothesis was rejected when the upper-tail Monte Carlo p-value was ≤0.05. The current version of MDR used in this project allows for the incorporation and adjustment of multiple covariates [38].

To remove the covariate effect, we integrated two sampling methods (i.e., over- and under-sampling). This approach is computationally efficient, thus allowing for adjustment of multiple covariates without significantly increasing computational burden.

Visualization of Interaction Models Using Interaction Entropy Algorithms, Hierarchical Interaction entropy algorithm, based on information theory, is a method to verify, visualize, and interpret combination effects identified by LR and MDR [34,39-42]. Orange software was used to perform interaction entropy analysis among selected chemokine-associated SNPs in relation to PCA discreet outcomes [43]. In addition, measures of interaction were used to build both interaction entropy graphs and dendrograms, useful for visualizing and interpreting interactions among variables. Interaction entropy uses information gain (IG) to gauge whether interactions between two or more factors provide more information about cancer outcomes relative to each factor considered independently. Individual, as well as, all possible pairwise loci are assigned an IG percentage score in relation to disease risk or aggressiveness (scores <5% are typical). Pairwise SNP combinations were deemed important if the pairwise IG was greater than the IG for each individual locus [e.g., $(IG_{SNP\_1+SNP\_2} > IG_{SNP\_1})$ and $(IG_{SNP\_1+SNP\_2} > IG_{SNP\_2})$]. Interactions can be further visualized using an interaction entropy graph (e.g., as in FIG. 1), which uses a similar color-coding scheme to readily interpret interactions. Strongly interacting factors were coded either "high" or "low", indicating high and medium levels of synergistic effects on outcomes, respectively. Weakly interacting factors were coded to denote high or modest levels of redundancy between markers, respectively. Narrow lines in the graph represents independence and a midway point between synergy and redundancy.

Analysis of Gene Interactions Using Multi-Factor Dimensionality Reduction (MDR)

MDR modeling was used to exhaustively evaluate and validate main effects and 13,244 epistasis models in relation to PCA, after adjusting for age group (Tables 7-9). In the total population consisting of both men from the U.S. and Jamaica, the CCL5 rs381655 loci was the best one factor model with 100% and 59.4% cross validation consistency and accuracy prediction scores Permutation testing P=0.001), respectively (Table 7). Although the two-way interaction between CCR4 rs6550178-CCL5 rs3817655 was statistically significant, the combined information gain score (IG=0.71%) was not greater than each individual SNP. In addition, the cross validation consistency score for the three-way interaction model did not meet the established criteria (i.e., CVC≥80%).

Similar to the total population, the CCL5 rs3817655 SNP was selected as the best MDR single factor predictor of prostate cancer risk in the total population and among U.S. men with permutation testing p-values of 0.0001, as shown in Table 7 and 8. In addition, significant two- and three-way interactions were observed between or among CCL24 rs2302004-CCL5 rs3817655 (permutation testing P=0.003) and CCR5 rs2227010-CCR7 rs3136687-CXCR5 rs523604 (permutation P=0.001) in relation to prostate cancer risk among U.S. men. However, the three-way interaction model had a higher cross-validation consistency (80% versus 70%) and prediction accuracy scores (65.78% versus 59.57%) when compared to the two-way models (Table 8). Based on information gain theory, the three-way interaction appears to be primarily driven by a synergistic interaction between CXCR5 rs523604 and CCR5 rs2227010, as demonstrated in FIG. 1.

In terms of the Jamaican men, the best one factor model was CCR9 rs2286486 with a 90% CVC and 58.6% prediction accuracy; however, this loci only reached marginal significance after adjusting for multiple comparisons (permutation testing P=0.061; Table 9). Although the three-factor model reached statistical significance, it had a low CVC score that did not meet our minimum requirement for further consideration.

Tables 7-9. Evaluation of Main Effects and Interactions Among Chemokine SNPs as Predictors of PCA Using MDR after Adjustments for Age.

TABLE 7

For U.S. and Jamaican Men

| Best Model | Cross Validation Consistency CVC | Accuracy (ATA) | P-value |
|---|---|---|---|
| One Factor | | | |
| CCL5 rs3817655 | 10 | 0.5945 | 0.001 |
| Two Factor | | | |
| CCL5 rs3817655 CCR4 rs6550178 | 9 | 0.6086 | 0.001 |
| Three Factor | | | |
| CCR7 rs3136687 CCR5 rs2227010 CXCR5 rs523604 | 7 | 0.6644 | 0.001 |

TABLE 8

For U.S. Men only

| Best Model | Cross Validation Consistency CVC | Accuracy (ATA) | P-value |
|---|---|---|---|
| One Factor | | | |
| CCL5 rs3817655 | 10 | 0.5799 | 0.001 |
| Two Factor | | | |
| CCL5 rs3817655 CCL24 rs2302004 | 7 | 0.5957 | 0.003 |
| Three Factor | | | |
| CCR7 rs3136687 CCR5 rs2227010 CXCR5 rs523604 | 8 | 0.6578 | 0.001 |

TABLE 9

For Jamaican Men Only

| Best Model Jamaican Men | Cross Validation Consistency CVC | Average Testing Accuracy (ATA) | Permutation P-value |
|---|---|---|---|
| One Factor | | | |
| CCR9 rs2286486 | 9 | 0.5858 | 0.061 |
| Two Factor | | | |
| CCR9 rs2286486 CCR7 rs3136689 | 4 | 0.5432 | 0.329 |
| Three Factor | | | |
| CCR6 rs3093024 CCR4 rs6550178 CXCR7 rs7559855 | 4 | 0.5905 | 0.017 |

REFERENCES

1. American Cancer, S. et al. (2012) Cancer Facts and Figures 2012. American Cancer Society, Atlanta, Ga.
2. American Cancer, S. et al. (2011) Cancer Facts & Figures for African Americans 2011-2012. American Cancer Society, Atlanta.
3. Ferlay, J. et al. (2010) Estimates of worldwide burden of cancer in 2008: GLOBOCAN 2008. International journal of cancer, 127, 2893-917.
4. Luster, A. D. et al. (1998) Chemokines-chemotactic cytokines that mediate inflammation. The New England journal of medicine, 338, 436-45.
5. Rollins, B. J. et al. (1997) Chemokines. Blood, 90, 909-28.
6. Strieter, R. M. et al. (2005) CXC chemokines in angiogenesis. Cytokine & growth factor reviews, 16, 593-609.
7. Strieter, R. M. et al. (1995) The functional role of the ELR motif in CXC chemokine-mediated angiogenesis. The Journal of biological chemistry, 270, 27348-57.
8. Chang, C. C. et al. (2009) Stromal cell-derived factor-1 but not its receptor, CXCR4, gene variants increase susceptibility and pathological development of hepatocellular carcinoma. Clinical chemistry and laboratory medicine: CCLM/FESCC, 47, 412-8.
9. Hirata, H. et al. (2007) CXCL12 G801A polymorphism is a risk factor for sporadic prostate cancer susceptibility.

Clinical cancer research: an official journal of the American Association for Cancer Research, 13, 5056-62.
10. Liou, J. M. et al. (2008) RANTES-403 polymorphism is associated with reduced risk of gastric cancer in women. Journal of gastroenterology, 43, 115-23.
11. Vindrieux, D. et al. (2009) Emerging roles of chemokines in prostate cancer. Endocrine-related cancer, 16, 663-73.
12. Soria, G. et al. (2009) The CCL5/CCR5 Axis in Cancer. Human Press, New York.
13. Taichman, R. S. et al. (2002) Use of the stromal cell-derived factor-1/CXCR4 pathway in prostate cancer metastasis to bone. Cancer research, 62, 1832-7.
14. Moore, B. B. et al. (1999) Distinct CXC chemokines mediate tumorigenicity of prostate cancer cells. The American journal of pathology, 154, 1503-12.
15. Reiland, J. et al. (1999) CXC-chemokines stimulate invasion and chemotaxis in prostate carcinoma cells through the CXCR2 receptor. The Prostate, 41, 78-88.
16. Vaday, G. G. et al. (2006) Expression of CCL5 (RANTES) and CCR5 in prostate cancer. The Prostate, 66, 124-34.
17. Coussens, L. M. et al. (2002) Inflammation and cancer. Nature, 420, 860-7.
18. Manes, S. et al. (2003) CCR5 expression influences the progression of human breast cancer in a p53-dependent manner. The Journal of experimental medicine, 198, 1381-9.
19. Zhernakova, A. et al. (2006) Genetic variants of RANTES are associated with serum RANTES level and protection for type 1 diabetes. Genes and immunity, 7, 544-9.
20. An, P. et al. (2002) Modulating influence on HIV/AIDS by interacting RANTES gene variants. Proceedings of the National Academy of Sciences of the United States of America, 99, 10002-7.
21. Saenz-Lopez, P. et al. (2008) Genetic polymorphisms of RANTES, IL1-A, MCP-1 and TNF-A genes in patients with prostate cancer. BMC Cancer, 8, 382.
22. Weng, C. J. et al. (2010) Effect of CC chemokine ligand 5 and CC chemokine receptor 5 genes polymorphisms on the risk and clinicopathological development of oral cancer. Oral oncology, 46, 767-72.
23. Duell, E. J. et al. (2006) Inflammation, genetic polymorphisms in proinflammatory genes TNF-A, RANTES, and CCR5, and risk of pancreatic adenocarcinoma. Cancer epidemiology, biomarkers & prevention: a publication of the American Association for Cancer Research, cosponsored by the American Society of Preventive Oncology, 15, 726-31.
24. Purdue, M. P. et al. (2011) Variation in innate immunity genes and risk of multiple myeloma. Hematological oncology, 29, 42-6.
25. Enjuanes, A. et al. (2008) Genetic variants in apoptosis and immunoregulation-related genes are associated with risk of chronic lymphocytic leukemia. Cancer research, 68, 10178-86.
26. Kidd, L. C. et al. (2011) No association between variant N-acetyltransferase genes, cigarette smoking and Prostate Cancer susceptibility among men of African descent. Biomarkers in cancer, 2011, 1-13.
27. Jackson, M. D. et al. (2012) Associations of whole-blood fatty acids and dietary intakes with prostate cancer in Jamaica. Cancer causes & control: CCC, 23, 23-33.
28. Manolio, T. A. et al. (2009) Finding the missing heritability of complex diseases. Nature, 461, 747-53.
29. McCarthy, M. I. et al. (2008) Genome-wide association studies for complex traits: consensus, uncertainty and challenges. Nature reviews. Genetics, 9, 356-69.
30. Steemers, F. J. et al. (2005) Illumina, Inc. Pharmacogenomics, 6, 777-82.
31. Menashe, I. et al. (2008) PGA: power calculator for case-control genetic association analyses. BMC Genet, 9, 36.
32. Greene, C. S. et al. (2009) Spatially Uniform ReliefF (SURF) for computationally-efficient filtering of gene-gene interactions. BioData Min, 2, 5.
33. Moore, J. H. et al. (2010) Bioinformatics challenges for genome-wide association studies. Bioinformatics, 26, 445-55.
34. Moore, J. H. et al. (2006) A flexible computational framework for detecting, characterizing, and interpreting statistical patterns of epistasis in genetic studies of human disease susceptibility. J. Theor. Biol., 241, 252-261.
35. Andrew, A. S. et al. (2005) Concordance of multiple analytical approaches demonstrates a complex relationship between DNA repair gene SNPs, smoking, and bladder cancer susceptibility. Carcinogenesis, 1030-1037.
36. Hahn, L. W. et al. (2003) Multifactor dimensionality reduction software for detecting gene-gene and gene-environment interactions. Bioinformatics., 19, 376-382.
37. Moore, J. H. et al. (2004) Computational analysis of gene-gene interactions using multifactor dimensionality reduction. Expert. Rev. Mol. Diagn., 4, 795-803.
38. Gui, J. et al. (July 2010) A Simple and Computationally-Efficient Sampling Approach to Covariate Adjustment for Multifactor Dimensionality Reduction Analysis of Epistasis. Tentative Submission to BMC Bioinformatics.
39. McGill, W. L. et al. (1954) Multivariate information transmission. In Psychometrika, vol. 19, pp. 97-116.
40. Jakulin, A. et al. (2003) Analyzing attribute interations. Lecture Notes in Artificial Intelligence, 2838, 229.
41. Jakulin, A. et al. (2003) Attribute interactions in medical data analysis. Lecture Notes in Artificial Intelligence, 2780, 229.
42. Andrew, A. S. et al. (2006) Concordance of multiple analytical approaches demonstrates a complex relationship between DNA repair gene SNPs, smoking, and bladder cancer susceptibility. Carcinogenesis, 27, 1030-1037.
43. Demsar, J. et al. (2004) Orange: from experimental machine learning to interactive data mining. In Boulicaut, J. F., Esposito, F., Giannotti, F. and Pedreschi, D. (eds.), 8th European Conference on Principles and Practice Knowledge Discoveries in Databases. Springer, Pisa, Italy, vol. 3202, pp. 537-539.
44. Konig, J. E. et al. (2004) Analysis of the inflammatory network in benign prostate hyperplasia and prostate cancer. The Prostate, 58, 121-9.
45. Petersen, D. C. et al. (2008) No association between common chemokine and chemokine receptor gene variants and prostate cancer risk. Cancer epidemiology, biomarkers & prevention: a publication of the American Association for Cancer Research, cosponsored by the American Society of Preventive Oncology, 17, 3615-7.

46. Bracci, P. M. et al. (2010) Chemokine polymorphisms and lymphoma: a pooled analysis. Leukemia & lymphoma, 51, 497-506.
47. Blanpain, C. et al. (2001) A chimeric MIP-1alpha/RANTES protein demonstrates the use of different regions of the RANTES protein to bind and activate its receptors. Journal of leukocyte biology, 69, 977-85.
48. Fellay, J. et al. (2009) Common genetic variation and the control of HIV-1 in humans. PLoS genetics, 5

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
providing a blood sample comprising DNA from a subject of self-reported African descent who is suspected of being at risk of developing prostate cancer (PCa);
contacting the sample with oligonucleotide probes that are identical to at least 20 nucleotides of SEQ ID NO:1 and that terminate adjacent to a polymorphic site or encompass the polymorphic site to detect the genotype at rs1799988;
contacting the sample with oligonucleotide probes that are identical to at least 20 nucleotides of SEQ ID NO:6 and that terminate adjacent to a polymorphic site or encompass the polymorphic site to detect the genotype at rs2107538;
contacting the sample with oligonucleotide probes that are identical to at least 20 nucleotides of SEQ ID NO:7 and that terminate adjacent to a polymorphic site or encompass the polymorphic site to detect the genotype at rs3817655;
detecting a subject with a CC genotype at rs1799988, a subject without a GA or AA genotype at rs2107538, or a subject without a TA or AA genotype at rs3817655, using said oligonucleotide probes; and
detecting levels of Prostate Serum Antigen (PSA) in the blood sample from the subject.

2. The method of claim 1 further comprising performing an imaging study on the subject to detect the development of PCa and/or performing a prostate biopsy on the subject to detect cancerous cells.

3. The method of claim 1 further comprising administering a prophylactic treatment to the selected subject to decrease their risk of developing PCa.

4. The method of claim 1 further comprising administering a treatment for PCa to the selected subject.

5. The method of claim 1, wherein the subject is a patient having one or more risk factors associated with PCa.

6. The method of claim 5, wherein the risk factors associated with PCa include one or more of: age; race/ethnicity; nationality; family history; diet; obesity; lack of exercise; inflammation of the prostate; infection; and vasectomy.

7. The method of claim 1, wherein the subject has one or more of a grandfather, father, uncle, brother, or son who has or had PCa.

8. The method of claim 4, wherein the treatment is surgery; radiation therapy; or hormone therapy.

9. The method of claim 1, wherein detecting the genotype comprises sequencing.

10. The method of claim 1, wherein detecting the genotype comprises performing fluorescence polarization template-directed dye-terminator incorporation.

11. The method of claim 1, wherein the probes are labeled.

* * * * *

UNITED STATES PATENT AND TRADEMARK OFFICE
CERTIFICATE OF CORRECTION

PATENT NO.         : 9,863,002 B2
APPLICATION NO.    : 13/907779
DATED              : January 9, 2018
INVENTOR(S)        : La Creis Renee Kidd and Kevin Sean Kimbro Page 1 of 1

It is certified that error appears in the above-identified patent and that said Letters Patent is hereby corrected as shown below:

On the Title Page

Column 1 (Applicants), delete "Durhma," and insert -- Durham, --

Signed and Sealed this
Eighth Day of May, 2018

Andrei Iancu
*Director of the United States Patent and Trademark Office*

SEQUENCE LISTING

```
<160> NUMBER OF SEQ ID NOS: 11

<210> SEQ ID NO 1
<211> LENGTH: 62
<212> TYPE: DNA
<213> ORGANISM: Artificial
<220> FEATURE:
<223> OTHER INFORMATION: Synthetically generated primers

<400> SEQUENCE: 1
taatccagtg agaaaagccc gtaaataaac ctttcagacc agagatctat tctctagctt    60
at                                                                  62

<210> SEQ ID NO 2
<211> LENGTH: 62
<212> TYPE: DNA
<213> ORGANISM: Artificial
<220> FEATURE:
<223> OTHER INFORMATION: Synthetically generated primers

<400> SEQUENCE: 2
ggggatacgg ggagagtgga gaaaaagggg agcacagggt taatgtgaag tccaggatcc    60
cc                                                                  62

<210> SEQ ID NO 3
<211> LENGTH: 62
<212> TYPE: DNA
<213> ORGANISM: Artificial
<220> FEATURE:
<223> OTHER INFORMATION: Synthetically generated primers

<400> SEQUENCE: 3
tcattttgtg taacagaaac cctccctcct ctacccacct cttgctcctt gctgggcaga    60
tg                                                                  62

<210> SEQ ID NO 4
<211> LENGTH: 62
<212> TYPE: DNA
<213> ORGANISM: Artificial
<220> FEATURE:
<223> OTHER INFORMATION: Synthetically generated primers

<400> SEQUENCE: 4
ggaaagaaaa ttattggctg gctgccccca ctctccaaac catgaacttc catccccaca    60
tt                                                                  62

<210> SEQ ID NO 5
<211> LENGTH: 53
<212> TYPE: DNA
<213> ORGANISM: Artificial
<220> FEATURE:
<223> OTHER INFORMATION: Synthetically generated primers

<400> SEQUENCE: 5
```
agcagcaccg ccacgtggta gggcaagcca gcagacagga aagaccacca ctg      53

<210> SEQ ID NO 6
<211> LENGTH: 62
<212> TYPE: DNA
<213> ORGANISM: Artificial
<220> FEATURE:
<223> OTHER INFORMATION: Synthetically generated primers

<400> SEQUENCE: 6
taacatcctt ccatggatga gggaaaggag agtaagatct gtaatgaata agcaggaact   60
tt                                                                 62

<210> SEQ ID NO 7
<211> LENGTH: 62
<212> TYPE: DNA
<213> ORGANISM: Artificial
<220> FEATURE:
<223> OTHER INFORMATION: Synthetically generated primers

<400> SEQUENCE: 7
ttctggcttg gagcccttt g atccaacaga atgaggaaat gttctctcct taaaagccac   60
aa                                                                 62

<210> SEQ ID NO 8
<211> LENGTH: 62
<212> TYPE: DNA
<213> ORGANISM: Artificial
<220> FEATURE:
<223> OTHER INFORMATION: Synthetically generated primers

<400> SEQUENCE: 8
atgctcgaaa taaggttttt gcaaagctcc agccacaaca cgcagacctt ccaaggtggg   60
ca                                                                 62

<210> SEQ ID NO 9
<211> LENGTH: 62
<212> TYPE: DNA
<213> ORGANISM: Artificial
<220> FEATURE:
<223> OTHER INFORMATION: Synthetically generated primers

<400> SEQUENCE: 9
taacatcctt ccatggatga gggaaaggag agtaagatct gtaatgaata agcaggaact   60
tt                                                                 62

<210> SEQ ID NO 10
<211> LENGTH: 62
<212> TYPE: DNA
<213> ORGANISM: Artificial
<220> FEATURE:
<223> OTHER INFORMATION: Synthetically generated primers

<400> SEQUENCE: 10
acacctgtag gccttgaggg tgtagacctt agaagacaga aaaactgatc aggagatccc   60
tg                                                                 62

<210> SEQ ID NO 11
<211> LENGTH: 62
<212> TYPE: DNA
<213> ORGANISM: Artificial
<220> FEATURE:

```
<223> OTHER INFORMATION: Synthetically generated primers

<400> SEQUENCE: 11
tatgattgcc aacagcaccc ctcaagggct acttcctcca aatttctatg agaccttgaa    60
cc                                                                   62
```